(12) United States Patent
Teague et al.

(10) Patent No.: US 10,799,235 B2
(45) Date of Patent: Oct. 13, 2020

(54) SUTURING DEVICE FOR TREAMENT OF PELVIC FLOOR DISORDERS

(71) Applicant: Boston Scientific Scimed, Inc., Maple Grove, MN (US)

(72) Inventors: James A. Teague, Spencer, IN (US); Jeffrey Zerfas, Bloomington, IN (US); John Lingeman, Plainfield, IN (US); Christopher Green, Bloomington, IN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 827 days.

(21) Appl. No.: 13/966,767

(22) Filed: Aug. 14, 2013

(65) Prior Publication Data

US 2014/0052159 A1 Feb. 20, 2014

Related U.S. Application Data

(60) Provisional application No. 61/683,921, filed on Aug. 16, 2012.

(51) Int. Cl.
*A61B 17/04* (2006.01)
*A61B 17/062* (2006.01)
*A61B 17/00* (2006.01)

(52) U.S. Cl.
CPC ...... *A61B 17/0483* (2013.01); *A61B 17/0469* (2013.01); *A61B 17/0625* (2013.01);
(Continued)

(58) Field of Classification Search
CPC ............ A61B 17/0483; A61B 17/0625; A61B 17/0469; A61B 2017/047; A61B 2017/0472; A61L 317/0483
(Continued)

(56) References Cited

U.S. PATENT DOCUMENTS 4,312,337 A * 1/1982 Donohue ........... A61B 17/1796
606/103
5,059,207 A 10/1991 Shah
(Continued)

FOREIGN PATENT DOCUMENTS

EP 0941698 A1 9/1999
EP 2033583 A1 3/2009
(Continued)

OTHER PUBLICATIONS

"FIXT iPhone Book", C.R. Bard, Inc., 2011, 8 pages.
(Continued)

*Primary Examiner* — Diane D Yabut
*Assistant Examiner* — Majid Jamialahmadi
(74) *Attorney, Agent, or Firm* — Brake Hughes Bellermann LLP

(57) ABSTRACT

The invention relates to a suturing device used to place sutures inside the human body during various medical procedures. The suturing device includes an elongate body member, a needle deployment mechanism and a needle receiving portion. The elongate body member has a distal portion that defines an opening. The needle deployment mechanism is disposed at least partially within the elongate body member for moving a needle out of the opening at the distal portion of the elongate body member into a tissue; and the needle receiving portion is provided at the distal portion of the elongate body member to capture the needle. The needle receiving portion has a non-planar surface with walls that are non-parallel with respect to a longitudinal direction of the needle receiving portion such that the walls converge to form an aperture formed in the needle receiving portion to receive the needle.

19 Claims, 33 Drawing Sheets

(52) U.S. Cl.
CPC .............. *A61B 2017/00805* (2013.01); *A61B 2017/047* (2013.01); *A61B 2017/0472* (2013.01)

(58) Field of Classification Search
USPC .................. 606/145, 139, 148–150, 147
See application file for complete search history.

(56) References Cited

U.S. PATENT DOCUMENTS

| | | | |
|---|---|---|---|
| 5,474,568 A | 12/1995 | Scott | |
| 5,782,866 A | 7/1998 | Wenstrom, Jr. | |
| 6,048,351 A * | 4/2000 | Gordon | A61B 17/0469 112/169 |
| 6,475,135 B1 | 11/2002 | Levy | |
| 6,551,330 B1 * | 4/2003 | Bain | A61B 17/0469 606/144 |
| 6,955,643 B2 * | 10/2005 | Gellman | A61B 17/0469 600/104 |
| 9,451,952 B2 | 9/2016 | Ostrovsky et al. | |
| 2003/0078599 A1 | 4/2003 | O'Quinn et al. | |
| 2004/0015177 A1 | 1/2004 | Chu | |
| 2004/0138682 A1 * | 7/2004 | Onuki | A61B 17/0401 606/144 |
| 2005/0015101 A1 * | 1/2005 | Gibbens, III | A61B 17/0482 606/144 |
| 2006/0195121 A1 * | 8/2006 | Chu | A61B 17/0469 606/144 |
| 2006/0282094 A1 * | 12/2006 | Stokes | A61B 1/00087 606/144 |
| 2007/0270885 A1 | 11/2007 | Weinert et al. | |
| 2009/0131956 A1 | 5/2009 | Dewey et al. | |
| 2009/0171143 A1 | 7/2009 | Chu et al. | |
| 2009/0312772 A1 * | 12/2009 | Chu | A61B 17/0469 606/144 |
| 2011/0022063 A1 | 1/2011 | McClurg et al. | |
| 2011/0066165 A1 | 3/2011 | Skinlo et al. | |
| 2013/0253542 A1 | 9/2013 | Ostrovsky et al. | |

FOREIGN PATENT DOCUMENTS

| | | |
|---|---|---|
| WO | 2008/030893 A2 | 3/2008 |
| WO | 2011/008607 A1 | 1/2011 |
| WO | 2013/142680 A1 | 9/2013 |
| WO | 2014/028710 A1 | 2/2014 |

OTHER PUBLICATIONS

"FIXT Suturing Device", C.R. Bard, Inc., 2011, 4 pages.
International Search Report and Written Opinion received for PCT Patent Application No. PCT/US2013/055097, dated Dec. 3, 2013, 11 pages.
International Preliminary Report on Patentability received for PCT Patent Application No. PCT/US2013/055097, dated Feb. 26, 2015, 8 pages.
International Search Report and Written Opinion received for PCT Patent Application No. PCT/US2013/033290, dated Jun. 25, 2013, 15 pages.
International Preliminary Report on Patentability received for PCT Patent Application No. PCT/US2013/033290, dated Oct. 2, 2014, 10 pages.
Restriction Requirement received for U.S. Appl. No. 13/794,053, dated Dec. 4, 2014, 6 pages.
Response to Restriction Requirement received for U.S. Appl. No. 13/794,053, filed Jan. 30, 2015, 1 page.
Non-Final Office Action Received received for U.S. Appl. No. 13/794,053, dated Mar. 4, 2015, 6 pages.
Response to Non-Final Office Action received for U.S. Appl. No. 13/794,053, filed May 29, 2015, 7 pages.
Final Office Action Received received for U.S. Appl. No. 13/794,053, dated Sep. 25, 2015, 11 pages.
Response to Final Office Action for U.S. Appl. No. 13/794,053, filed Nov. 25, 2015, 8 pages.
Non-Final Office Action Received received for U.S. Appl. No. 13/794,053, dated Jan. 15, 2016, 9 pages.
Lazarou, George, "Vaginal Prolapse", eMedicineHealth.com, 2014, 3 pages.

* cited by examiner

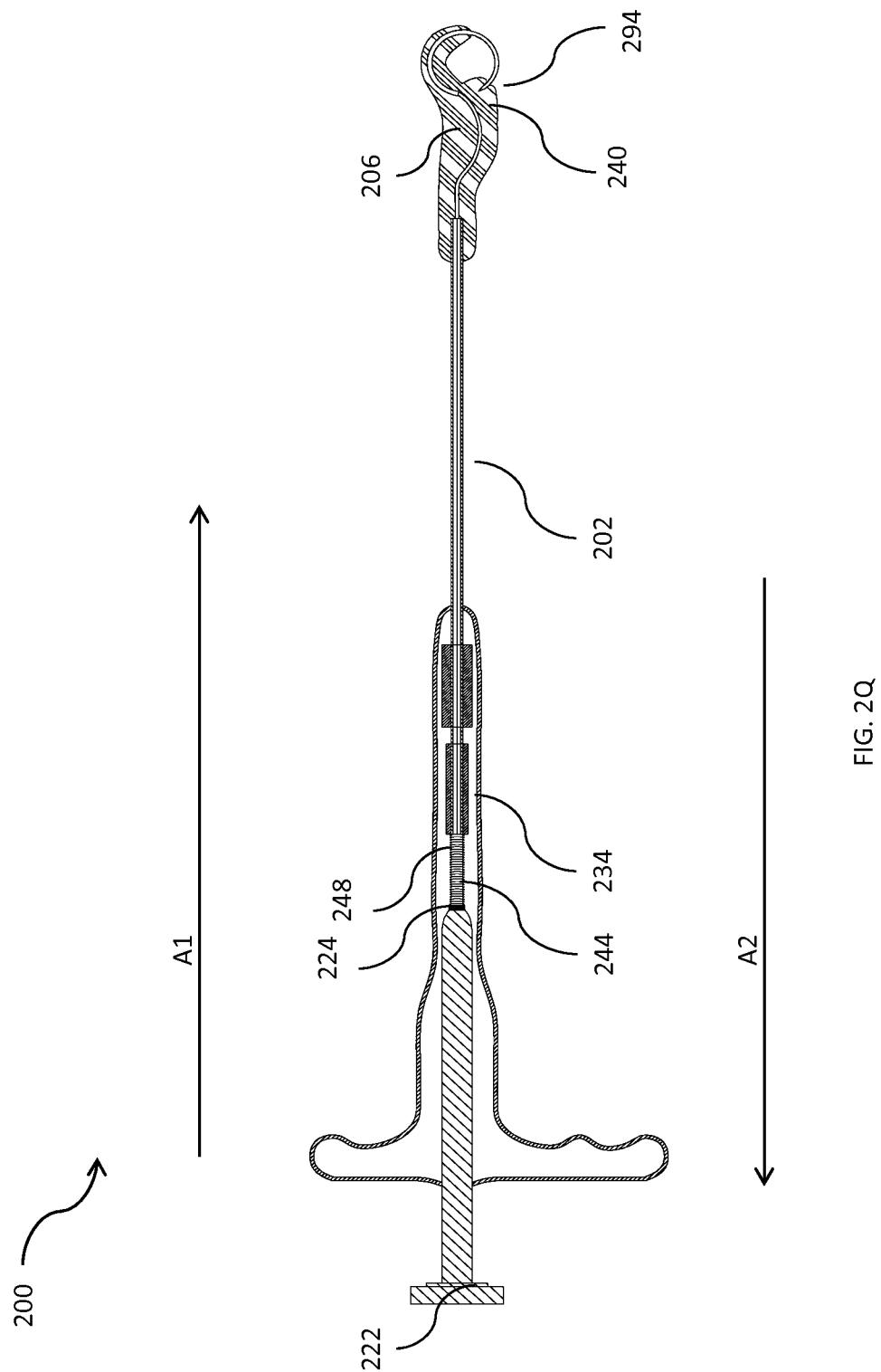

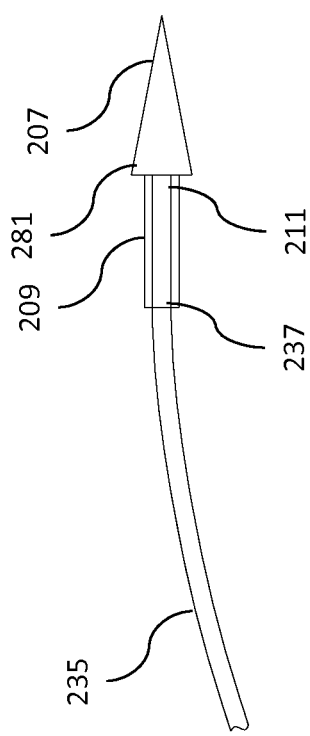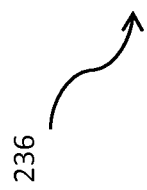
FIG. 2S

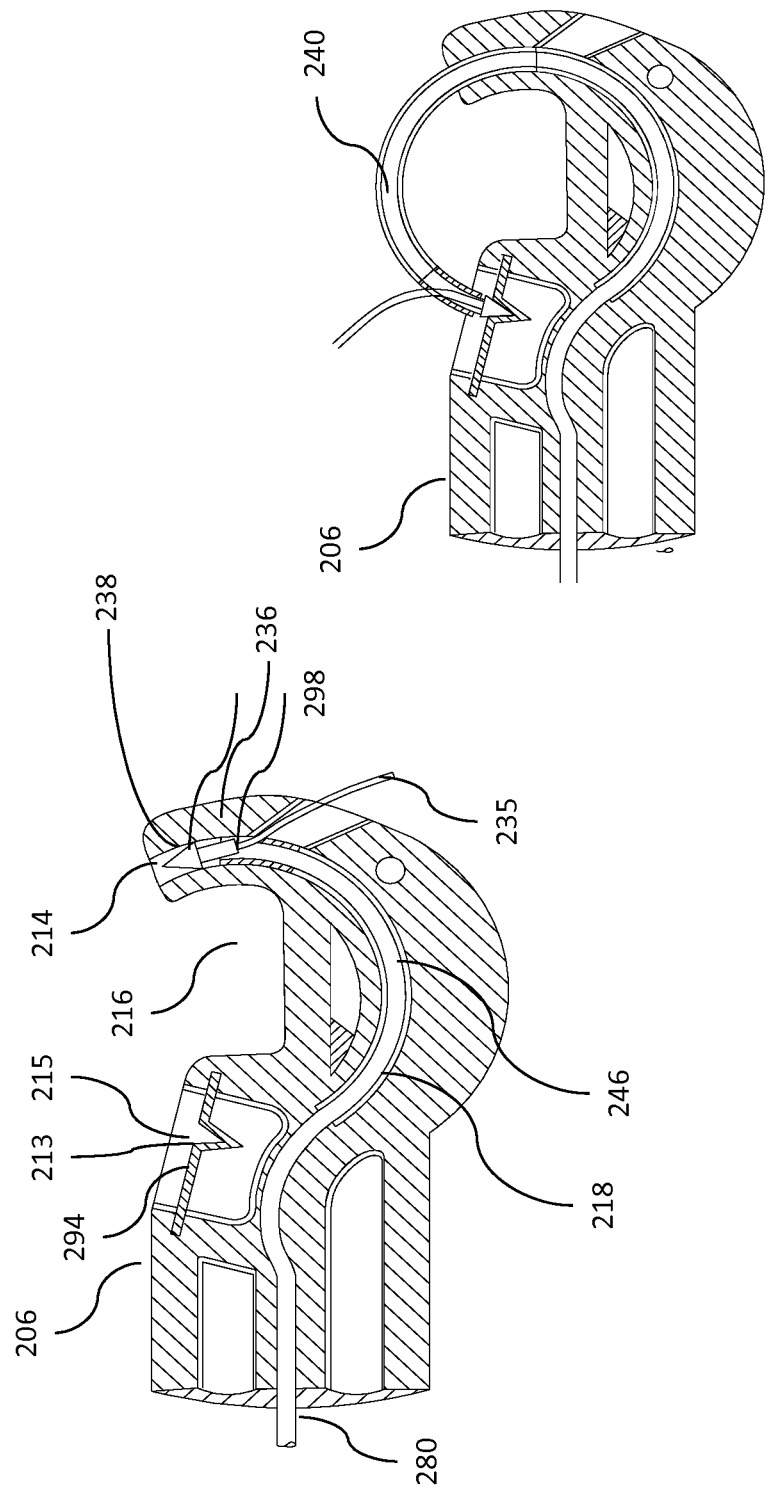

SUTURING DEVICE FOR TREAMENT OF PELVIC FLOOR DISORDERS

CROSS-REFERENCE TO RELATED APPLICATION

This application is a Nonprovisional of, and claims priority to, U.S. Patent Application No. 61/683,921, filed on Aug. 16, 2012, entitled "SUTURING DEVICE FOR TREATMENT OF PELVIC FLOOR DISORDERS", which is incorporated by reference herein in its entirety.

BACKGROUND

Field of Invention

The present invention generally relates to medical devices and procedures, particularly devices and methods for delivery and placement of medical implants into a patient's body.

Description of the Related Art

Suturing of body tissues may be time consuming and an important aspect of most surgical procedures. Many surgical procedures may be performed where it is necessary to make a large opening to expose the area, for instance, a bodily tissue of the human body, which requires a surgical repair. In various corrective surgeries or implant procedures, the bodily tissue must be returned to a normal anatomical position or placed in an improved position.

Suturing devices are used for these types of surgeries. These devices work on the mechanism of driving a needle loaded with a suture through the bodily tissues (to be sutured) and catching the needle after the suture has been placed. Such devices include a needle catch portion and a needle catch slot provided in the needle catch portion to catch the needle. In such devices, there is a chance of misalignment of the needle and the needle catch slot during the needle catch process when the needle is received in the needle catch slot. This misalignment can be due to various reasons, including effect of the bodily tissue on the component during passage through the tissue or ligament.

Existing suturing devices rely on a series of slots to make allowances for such misalignments. However, often the needle hits a solid land area between the slots and this can cause a misalignment between the needle and the slots. Further, the existing suturing devices have a blunt surface at the needle catch portion that may allow bodily tissues to get stuck inside the needle catch slot during the suturing. This would again cause a device misalignment.

Also, the overall size of the current suturing devices causes the physician to perform more dissection of bodily tissue in order to access the required tissues.

Therefore, there is a need for a device that allows for a minimally invasive surgical procedure and can avoid needle misalignment resulting from the needle hitting the land area between the slots and due to the blunt surface of the needle catch portion.

SUMMARY

The present invention discloses a suturing device including an elongate body member having a distal portion. The distal portion defines an opening. The suturing device further includes a needle deployment mechanism disposed at least partially within the elongate body member for moving a needle out of the opening at the distal portion of the elongate body member into a tissue. Also, a needle receiving portion is provided at the distal portion of the elongate body member to capture the needle. The needle receiving portion has a non-planar surface with walls that are non-parallel with respect to a longitudinal direction of the needle receiving portion such that the walls converge toward an aperture formed in the needle receiving portion to receive the needle.

In another embodiment, the invention discloses a suturing device including an elongate body member having a distal portion. The distal portion defines an opening. The elongate body member defines a lumen from the proximal portion to the opening. The suturing device further includes a needle deployment mechanism disposed at least partially within the elongate body member. The needle deployment mechanism includes a needle carrier disposed at the distal portion of the elongate body member and defines a channel for holding a needle. The needle deployment mechanism also includes an actuator configured to move the needle out of the opening at the distal portion of the elongate body member into a tissue. Also, a needle receiving portion is provided at the distal portion of the elongate body member to capture the needle. The needle receiving portion has a non-planar surface with walls that are non-parallel with respect to a longitudinal direction of the needle receiving portion such that the walls converge toward an aperture formed in the needle receiving portion to receive the needle.

In another embodiment, the present invention discloses a method including inserting a suturing device inside a patient's body. The suturing device includes an elongate body member, a needle deployment mechanism disposed at least partially within the elongate body member, and a needle receiving portion. The method further includes contacting a needle of the suturing device with the needle receiving portion by actuating the needle deployment mechanism such that the needle moves along a non-planar surface and into an aperture of the needle receiving portion and is received by the aperture. The method further includes suturing a bodily implant to a bodily tissue using a suture loaded on the suturing device. The bodily implant is coupled to the suture. The method also includes retracting the needle deployment mechanism after the needle is captured into the aperture.

BRIEF DESCRIPTION OF THE FIGURES

The invention and the following detailed description of certain embodiments thereof may be understood with reference to the following figures:

FIG. 2I is an enlarged cross-sectional view of a portion of a distal portion of the suturing device illustrating a rotation ring.

FIG. 2O is a view of a suturing device placed in a tubing shrink.

FIG. 2Q illustrates a deployed position of a suturing device.

FIG. 2S illustrates a perspective view of a needle to be used in some embodiments of the invention.

FIGS. 3A and 3B are enlarged cross-sectional views of a distal portion of an elongate body member with an actuator shown in retracted and deployed positions, respectively, in accordance with an embodiment of the present invention.

DETAILED DESCRIPTION

Detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

The terms "a" or "an," as used herein, are defined as one or more than one. The term "another," as used herein, is defined as at least a second or more. The terms "including" and/or "having", as used herein, are defined as comprising (i.e., open transition).

The terms proximal and distal described in relation to various medical devices, apparatuses, and components (as discussed in the subsequent text of the present invention) are referred with a point of reference. The point of reference, as used in this description, is a perspective of an operator. The operator may be a surgeon, a physician, a nurse, a doctor, a technician, and the like, who may perform the procedure of surgery through the patient's body orifice as described in the present invention. The term proximal refers to an area that is closest to the operator. The term distal refers to an area that is farthest from the operator. The patient can be a male, a female or any other mammal.

The present invention relates to a suturing device to be used for the treatment of a pelvic floor disorder such as genital prolapse, incontinence, cystoceles, rectoceles, and the like; however, it can be used for any procedure that requires sutures to be thrown remotely from outside the body. The surgical treatment of these disorders requires sutures to be placed through body tissues. These sutures may connect the pelvic organs to the pelvic floor or they can be used to place implants inside the patient's body. One such suturing device is disclosed by the present invention and described hereafter in conjunction with various drawings. A surgical procedure for suturing with the use of the disclosed device is also described.

Various embodiments of the suturing device are described herein. They should be considered as exemplary embodiments and should not be used to limit the scope of the invention.

Figure 1:
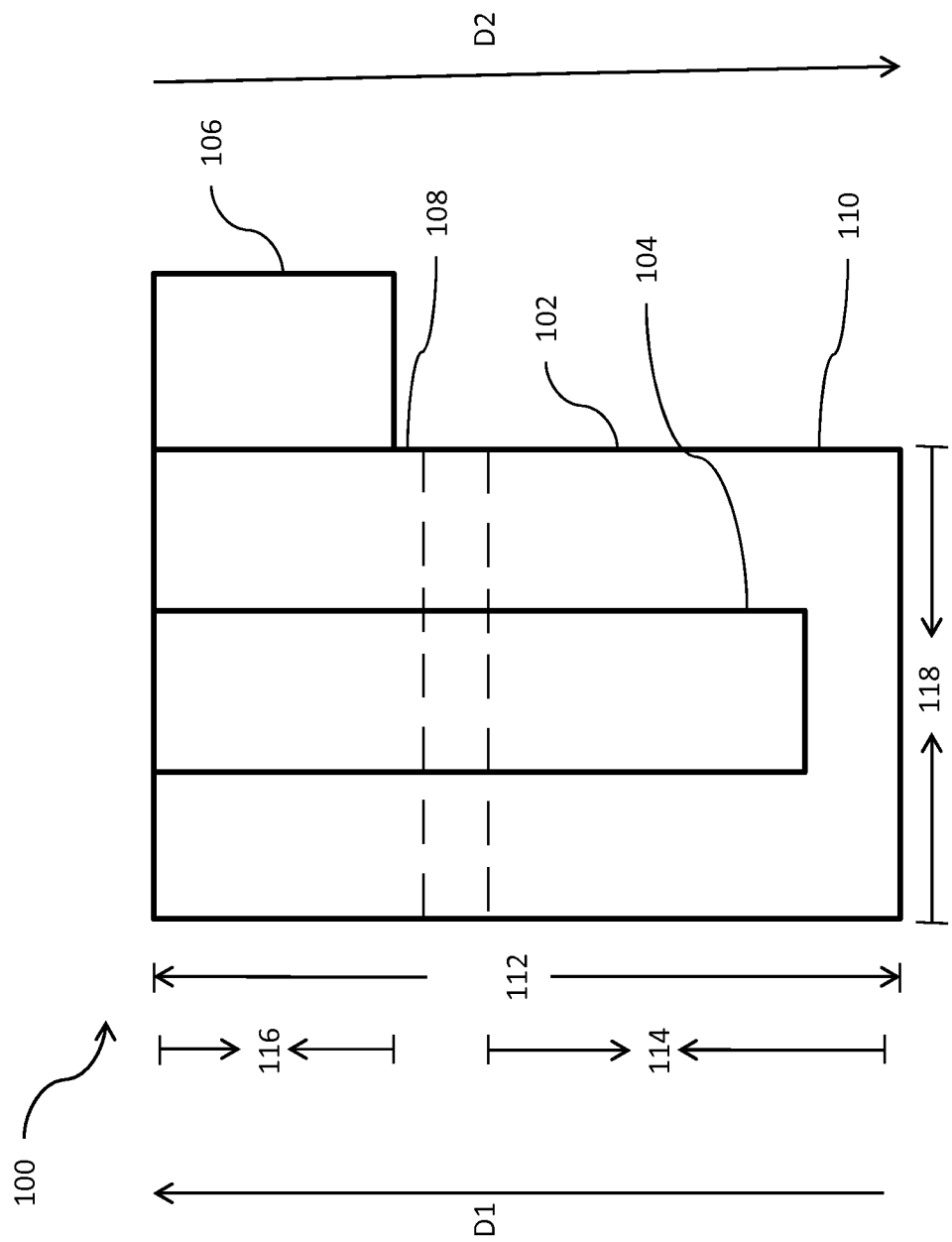
FIG. 1 is a schematic diagram of a suturing device, in accordance with an embodiment of the present invention.

FIG. 1 is a schematic diagram of a suturing device 100. The suturing device 100 is configured to be used to place sutures or to insert bodily implant (not shown) inside a patient's body (e.g., a female patient or a male patient). In some embodiments, the suturing device 100 is configured to be used to place sutures into the patient's body by insertion of the suturing device 100 into the patient's body from outside (e.g., insertion via a vaginal incision in the body of the patient, or insertion via a rectal incision in the body of the patient). The suturing device 100 may be used to suture tissues and ligaments together. In some embodiments, the suturing device 100 is configured to suture the bodily implant inside the patient's body. The suturing device 100 may be in various forms, a few of them are described herein with the help of various embodiments. As shown in FIG. 1, the suturing device 100 includes an elongate body member 102, a needle deployment mechanism 104, and a needle receiving portion 106. The needle deployment mechanism 104 is at least partially disposed within the elongate body member 102.

The elongate body member 102 includes a distal portion 108 and a proximal portion 110 with a length 112 of the elongate body member 102 extending between the distal portion 108 and the proximal portion 110 longitudinally. In accordance with various embodiments, the length 112 of the elongate body member 102 can vary based on the requirements. For example, in some embodiments of the invention, the length 112 may be between 280 mm and 360 mm (approximately 11.02 inches to 14.17 inches). Similarly, the length 114 of the proximal portion 110 of the elongate body member 102 can vary based on the requirements. For example, in some embodiments of the invention, the length 114 of the proximal portion 110 can vary between 130 mm and 150 mm (approximately 5.11 inches to 5.90 inches). The length 116 of the distal portion 108 of the elongate body member 102 may also vary. For example, in some embodiments, the length 116 of the distal portion 108 may range between 50 mm and 70 mm (approximately 1.96 inches to 2.75 inches).

The elongate body member 102 defines a width 118. The width 118 may vary based on requirements. In some embodiments, the width 118 may vary along the length 112 of the elongate body member. For example the width 118 of the elongate body member may be 20 mm across the proximal portion 110 and the width 118 can decrease to 11 mm or less toward the distal portion 108 of the elongate body member 102.

In various embodiments of the invention, the length 112 includes a working length (not shown) of the suturing device 100. The working length may be defined as a portion of the suturing device 100 that can be inserted into the patient's body during the surgical procedure. In some embodiments of the invention, the working length is different from the length 112 of the elongate body member 102 and the working length can range from about 90 mm to about 100 mm (approximately 3.54 inches to 4.00 inches). In various other embodiments, the working length can be different based on the requirements. The distal portion 108 of the elongate body member 102 defines an opening (not shown). The dimensions of various lengths as mentioned above are exemplary and various other dimensions are also possible. It must be understood and recognized that these dimensions may attribute a downsized profile to the suturing device 100, thereby enabling the physician to perform less dissection in order to access the required tissues.

The elongate body member 102 further includes a handle (not shown) that is configured to be held by an operator while performing a surgical procedure. In some embodiments of the invention, the width of the handle (not shown) may vary from 70 mm to 90 mm (approximately 2.75 inches to 3.54 inches). In some other embodiments, various other dimensions of the handle are also possible. In some embodiments, the handle forms an integral part of the elongate body member 102 and extend from the elongate body member 102 proximally. In some other embodiments, the handle may be a separate component and can be mechanically coupled to the elongate body member 102 at the proximal portion 110. In some embodiments of the invention, the handle is provided with a thumb-tab to increase the efficiency of the handle. A physician or a user can hold the handle by placing his finger or thumb on the thumb tab. The elongate body member 102 defines a lumen (not shown) extending from the proximal portion 110, running across the length 112 of the elongate body member 102 and culminating into the opening at the distal portion 108 of the elongate body member 102. The lumen defines an inner diameter of the elongate body member 102. The lumen of the elongate body member 102 is configured to receive and house at least some other elements and portions of the suturing device 100. For example, the elongate body member 102 can be configured to house at least some portion of the needle deployment mechanism 104 within a space formed within the lumen.

The distal portion 108 of the elongate body member 102 includes a protuberance (not shown) and a curved portion (not shown). The lumen of the elongate body member 102 extends through the curved portion and abuts at the opening of the distal portion 108 of the elongate body member 102. The curved portion also defines a second opening (not shown) for receiving a tissue.

The needle deployment mechanism 104 is disposed at least partially within the elongate body member 102. The needle deployment mechanism 104 is configured to move a needle (not shown), which is coupled to the needle deployment mechanism 104 at the distal portion 108 out of the opening of the elongate body member 102 into a tissue. The opening allows movement of the needle out of the elongate body member 102. The needle deployment mechanism 104 moves the needle between a retracted position and a deployed position. The retracted and the deployed positions are explained later.

The needle deployment mechanism 104 includes a needle carrier (not shown) and an actuator (not shown). The needle carrier is disposed at the distal portion 108 of the elongate body member 102 of the suturing device 100 within the lumen as described above. In some embodiments, a distal portion 108 of the needle carrier defines a channel (not shown) for holding the needle. In some other embodiments, the distal portion 108 of the needle carrier may include multiple channels or slots to hold multiple needles. In some embodiments, the channel may extend along the distal portion 108 of the carrier only. In some other embodiments, the channel may extend along an entire length of the carrier.

The actuator is disposed at the proximal portion 110 of the elongate body member 102 of the suturing device 100. In some embodiments, the actuator may extend from the proximal portion 110 to a medial portion and may also extend to the distal portion 108, in some embodiments. The actuator is configured to move the needle out of the opening at the distal portion 108 of the elongate body member 102. The actuator is connected to the needle carrier. The actuator can be either in a retracted position (not shown) or in a deployed position (not shown). In the deployed position, the actuator causes the needle carrier to extend out of the lumen of the elongate body member 102. Various types of actuating mechanisms may be deployed within or coupled to the actuator for moving the needle out of the opening. Some embodiments with exemplary actuating mechanisms and specific designs of actuators are discussed in conjunction with FIG. 2 below. In some embodiments, the retracted position of the actuator may also be referred to as the retracted position of the suturing device 100 and similarly, the deployed position of the actuator may also be referred to as the deployed position of the suturing device 100 interchangeably throughout this document, and without any scope limitations.

The suturing device 100 includes the needle receiving portion 106 provided at the distal end of the elongate body member 102. In some embodiments, the needle carrier is configured to contact at least a portion of the needle receiving portion 106. The needle receiving portion 106 includes a non-planar surface (not shown) with walls that converge to form an aperture (not shown) in the needle receiving portion 106 to receive the needle. The walls of the needle receiving portion 106 are angled with respect to an axial direction of the needle receiving portion 106 such that the walls form an acute angle with the axial direction of the needle receiving portion 106. This implies that the walls of the needle receiving portion 106 are not parallel with the longitudinal axis of the needle receiving portion 106. For example, the angle may be 30 degree or 40 degree or any other angle as required for an appropriate procedure and needle alignment with the needle receiving portion 106. In some embodiments, the non-planar surface can be a concave, substantially concave, conical or substantially conical.

In some embodiments, the walls of the non-planar surface are angled with respect to the axial direction in such a manner that there is a gradual decrease in a diameter of a hollow space created by the non-planar surface. This is configured to receive the needle in a gradual manner and avoid misalignment. For example, in case of the conical non-planar surface, the diameter of the hollow space created by the walls of the conical surface decreases gradually toward an aperture formed at the bottom of the non-planar surface. Therefore, the needle that is received within the aperture through the conical non-planar surface gradually moves downward toward the aperture and reduces or avoids a chance of misalignment of the needle with the aperture. Therefore, a device misalignment can be avoided. In some embodiments, the suturing device 100 may increase misalignment correction area by 25%.

In some embodiments, the needle receiving portion 106 includes radial slots provided on an inner surface (walls) of the needle receiving portion 106. The walls of the needle receiving portion 106 surrounding the radial slots are configured to move from a first position to a second position (illustrated in FIG. 3E later). This generates a spring action in the walls. The spring action of the radial slots allows the aperture to open and allow entry of the needle into the aperture. The spring action of the radial slots further facilitates closing of the aperture after the needle has entered the aperture. The closing of the aperture allows capture of the distal portion of the needle within the aperture. In accordance with other embodiments, the walls around the aperture (provided in the needle receiving portion 106) can be made of a flexible material that are configured to flexibly open or close the aperture based on a push or pull force exerted by the needle on the aperture. In some other embodiments, the needle receiving portion 106 may also include a spring or any other resilient material that is configured to flexibly open or close the aperture.

In accordance with an embodiment, the needle receiving portion 106 includes a single aperture configured to receive the needle. In other embodiments, the needle receiving portion 106 includes a plurality of apertures. In some embodiments, each of the apertures may be associated with a non-planar surface such as a conical surface to ensure that receipt of needle into the apertures will be preceded through a gradual entry along the non-planar surface. In some other embodiments, at least one of the apertures may be associated with a non-planar surface such as a conical surface to ensure that the receipt of needle into the at least one of the apertures will be preceded through a gradual entry along the non-planar surface. Further, in such embodiments, the plurality of non-planar surfaces and the plurality of apertures may be provided adjacent to one another.

In some embodiments of the invention, the needle receiving portion 106 includes a penetration depth controller to control penetration depth of the needle. The penetration depth controller may be an adaptor placed proximate to the needle carrier at the distal end of the elongate body member 102 of the suturing device 100. The adaptor prevents the tissue from entering the second opening thus controlling the depth of bite of the needle carrier. This is further described later in conjunction with FIG. 6.

Having described the suturing device 100 above, an overview of the interworking and structural cooperation between various portions or elements of the suturing device 100 is provided below.

In a general aspect, at least a portion of the elongate body member 102 of the suturing device 100 coupled to the suture is inserted into a body of a patient. In some embodiments, the needle carrier of the needle deployment mechanism 104 can be configured to slidably move through the lumen and configured to hold the needle. The needle carrier is further configured to move into at least a portion of the needle receiving portion 106 along with the needle in the deployed position. The needle carrier that is slidably disposed along the lumen of the elongate body member in the retracted position can be actuated such that the needle moves through a bodily tissue into the body of the patient.

In some embodiments, the actuator is configured to actuate the suturing device 100 to the deployed position from the refracted position. The actuator moves the needle carrier and the needle along the direction D1 and back to the retracted position from the deployed position by moving the needle carrier along the direction D2.

In some embodiments, actuating can include moving the suturing device 100 in the direction D1. The needle carrier can be moved slidably into the lumen in the direction D1 along the lumen and away from the proximal portion 110 of the elongate body member 102, and toward the needle receiving portion 106 of the suturing device 100 until the needle (coupled to the needle carrier) has moved into the non-planar surface. In some embodiments, the suture is loaded in the distal portion 108 of the elongate body member 102. The distal portion 108 defines the opening through which the needle comes out of the lumen when the suturing device 100 is actuated along the direction D1. In some embodiments, the aperture acts as a capture slot for the needle when it moves toward the needle receiving portion 106 on being actuated along the direction D1.

In some embodiments, the suturing device 100 is placed such that the bodily tissue (to be sutured) is present between the distal portion 108 of the elongate body member 102 of the suturing device 100 and the needle receiving portion 106 of the suturing device 100. When the needle is actuated along direction D1, it passes through the second opening (where the bodily tissue is placed) and moves toward the aperture of the needle receiving portion 106. When the needle enters the needle receiving portion 106, it is received by the aperture in the non-planar surface of the needle receiving portion 106. The radial slots along the walls of the non-planar surface move from the first position to the second position (illustrated later in FIG. 3E) as a result of a push force exerted by the needle onto the walls of the non-planar surface.

In some embodiments, when the walls surrounding the radial slots move to the second position, a space is created for the needle to enter the aperture. In some embodiments, the needle can have a dimension greater than the aperture diameter. When the needle enters the aperture, the radial slots move back to the first position, thereby capturing the needle into the aperture. The suture that is coupled to the needle is thereby effectively passed through the bodily tissue (the suture is coupled to the needle; therefore it will pass through the bodily tissue along with the needle). When the needle is captured into the aperture of the needle receiving portion, the suture is effectively passed through the tissue.

In some embodiments, actuating can include moving the suturing device 100 in the direction D2. The needle carrier can be moved slidably into the lumen in the direction D2 along the lumen and toward the proximal portion 110 of the elongate body member 102, and away from the needle receiving portion 106 of the suturing device 100 until the needle carrier has moved out of the needle receiving portion 106. In some embodiments, the actuator as discussed above can be configured to move the suturing device 100 back and forth along the direction D1 and D2.

Figure 2A:
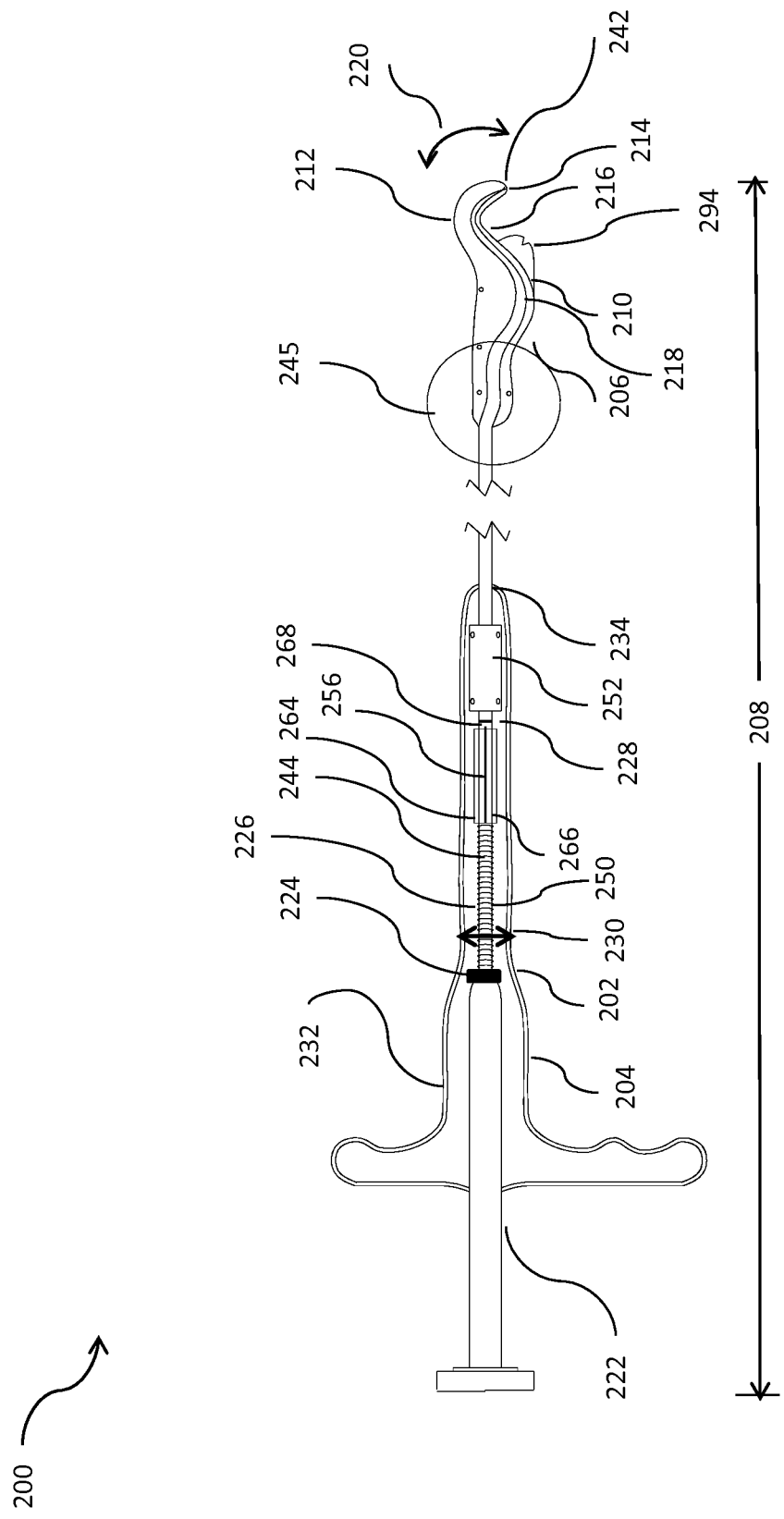
FIG. 2A is a cut away view of an embodiment of a suturing device, in accordance with an embodiment of the present invention.

FIGS. 2A-2S illustrates and elaborates various structural components of a suturing device 200, in accordance with some embodiments.

FIG. 2A is a perspective view of the suturing device 200, in accordance with an embodiment of the present invention. In accordance with this embodiment of the invention, the suturing device 200 includes an elongate body member 202, a needle deployment mechanism 234 and a needle receiving portion 294. The needle deployment mechanism 234 is at least partially disposed within the elongate body member 202.

The elongate body member 202 of the suturing device 200 includes a proximal portion 204 and a distal portion 206 with a length 208 of the elongate body member 202 extending between the proximal portion 204 and the distal portion 206 longitudinally. The distal portion 206 of the elongate body member 202 includes a distal end 242 of the suturing device 200. The distal portion 206 of the elongate body member 202 includes a protuberance 210 and a curved portion 212. The curved portion 212 defines an opening 214 at the distal portion 206 of the elongate body member 202. The curved portion 212 also defines a second opening 216 for receiving a tissue. The curved portion 212 defines a channel 218 which has a curved profile 220 and its cross-section is substantially circular in nature.

In some embodiments of the invention, the distal portion 206 of the elongate body member 202 may be or be referred to as the distal portion 206 of the suturing device 200. The distal portion 206 includes the distal end 242.

In accordance with the illustrated embodiment of FIG. 2A, the elongate body member 202 of the suturing device 200 includes a handle 222, a bearing 224 at the proximal portion 204 and a lumen 226 defined along the length 208 of the elongate member.

In some embodiments of the invention, the channel 218 may be a part of the lumen 226.

The handle 222 is configured to be held by an operator while performing a surgical procedure. In some embodiments, the handle 222 forms an integral part of the elongate body member 202 and extends from the elongate body member 202 proximally. In some other embodiments, the handle 222 may be a separate component and can be mechanically coupled to the elongate body member 202 at the proximal portion 204. In some embodiments, the handle 222 can include a thumb-tab to assist the operator while performing the surgical procedure. In some embodiments, the handle 222 may be configured so that to aid in actuation of the suturing device 200.

The proximal portion 204 of the elongate body member 202 includes the bearing 224. The bearing 224 is configured to couple the handle 222 of the elongate body member 202 to the needle deployment mechanism 234 of the suturing device 200. The needle deployment mechanism 234 is further described below.

The lumen 226 extends from the proximal portion 204, runs across the length 208 of the elongate body member 202 and culminates into the opening 214 at the distal portion 206 of the elongate body member 202. The lumen 226 forms a first cylindrical surface 228 and defines an inner diameter 230 of the elongate body member 202. It must be appreciated that the inner diameter may be constant or varying along the length 208 of the elongate body member 202. The lumen 226 of the elongate body member 202 is configured to receive and house at least some other elements and portions of the device. For example, the elongate body member 202 houses at least some portion of the needle deployment mechanism 234 within a space formed within the lumen 226. In some embodiments of the invention, the inner diameter 230 of the elongate body member 202 can vary between 0.110 inches to 0.130 inches, thereby contributing to a downsized profile of the device and enabling a physician or an operator to place his fingers alongside the device during placement and allow for less dissection requirement. This may make the device minimally invasive in nature.

The needle deployment mechanism 234 is disposed at least partially within the elongate body member 202 and configured to move a needle 236 (shown in FIG. 2C later) which is coupled to a needle carrier 246 provided at the needle deployment mechanism 234 at the distal portion 206 of the elongate body member 202 out of the opening 214 of the elongate body member 202 into a tissue. The opening 214 allows movement of the needle 236 out of the elongate body member 202. The needle deployment mechanism 234 moves the needle carrier 246 and the needle 236 coupled thereto, between a retracted position and a deployed position. The retracted and the deployed positions or configurations are represented by numbers 238 and 240 and described later.

The needle deployment mechanism 234 extends longitudinally through the elongate body member 202 to the distal portion 206 of the elongate body member 202. The needle deployment mechanism 234 is configured to be coupled to the needle 236 (explained later in FIG. 2B). The needle deployment mechanism 234 is configured to move the needle 236 between the refracted position 238 and the deployed position 240.

The needle deployment mechanism 234 includes an actuator 244 and the needle carrier 246. The actuator 244 may include a spring 248, a spring tube 250, a shaft 252, a backstop washer 254 and a push-wire 256. The needle deployment mechanism 234 is coupled to the handle 222 of the elongate body member 202 by way of the bearing 224.

Figure 2B:
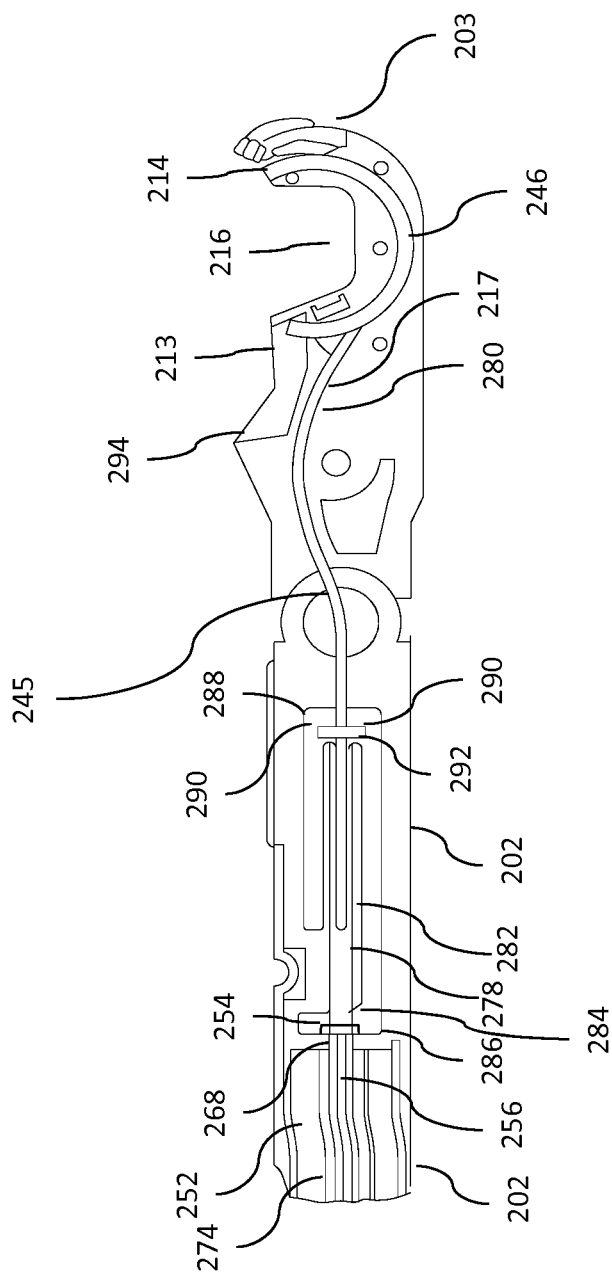
FIG. 2B is a cut away view schematic view of a distal portion of a suturing device in accordance with an embodiment of the present invention.
Figure 2C:
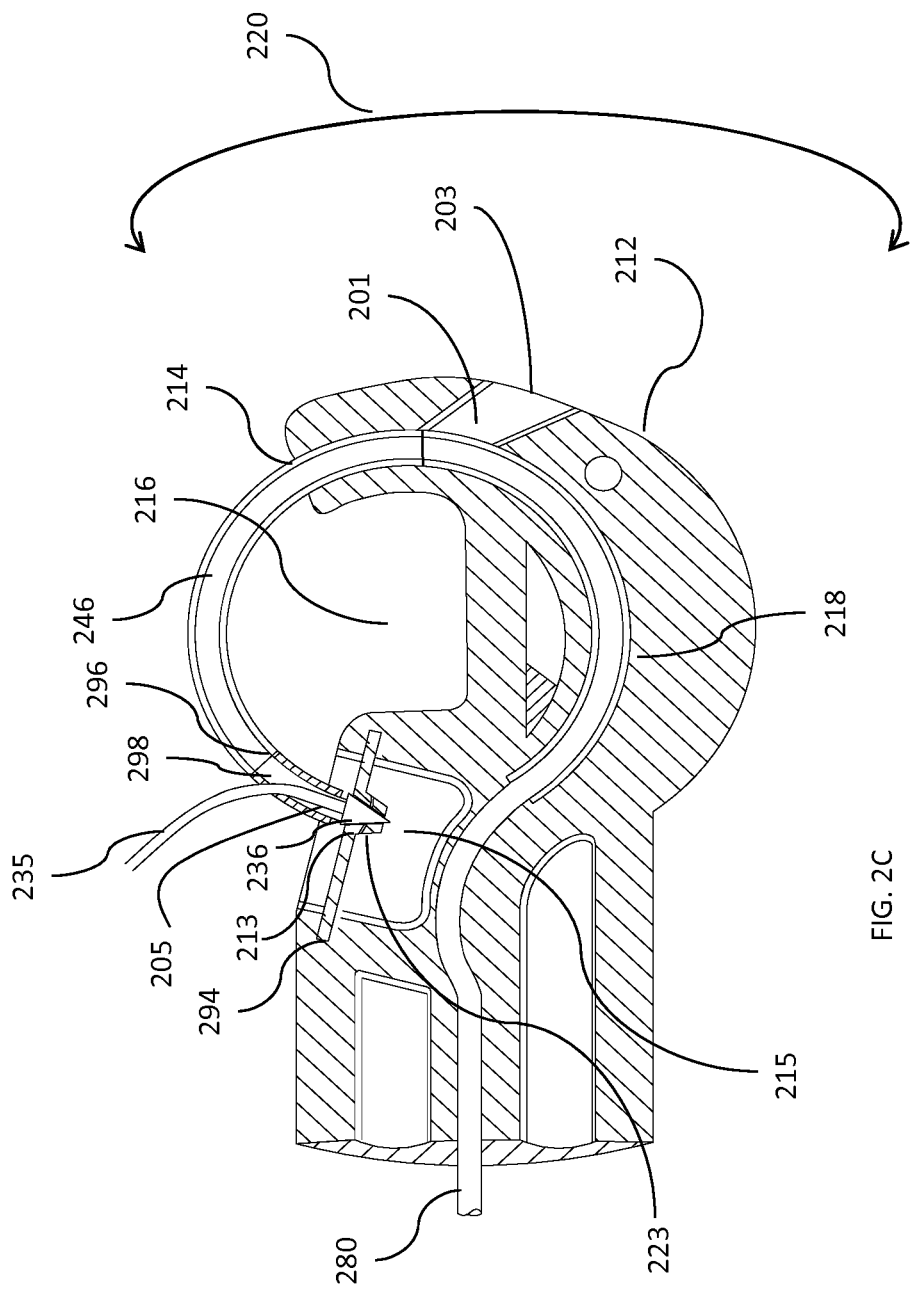
FIG. 2C is an enlarged cross-sectional view of the distal portion of the elongate body member of the suturing device of FIG. 2B.
Figure 2D:
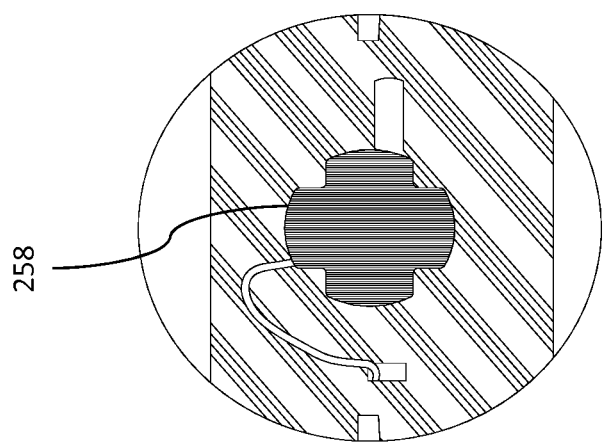
FIG. 2D is an enlarged cross-sectional view of a portion of a proximal portion of an elongate body member illustrating a handle clearance for the suturing device.
Figure 2E:
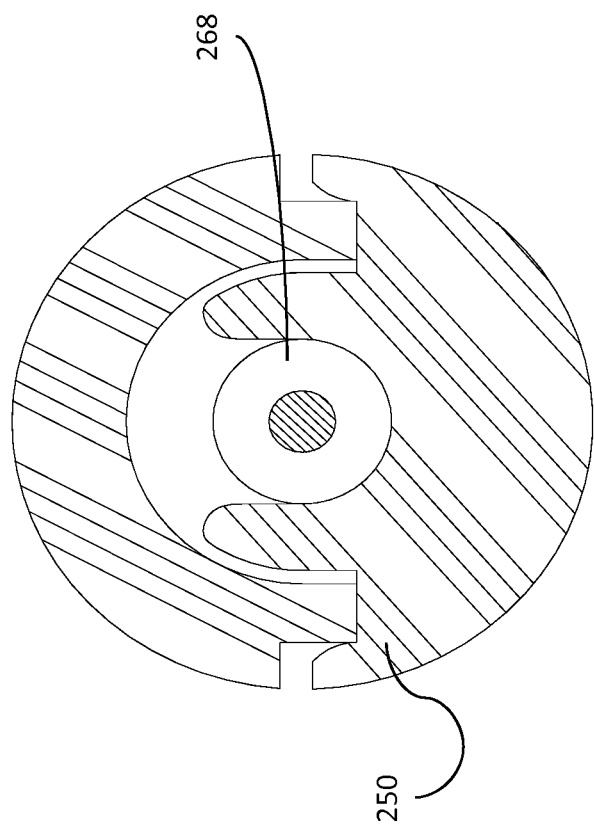
FIG. 2E is an enlarged cross-sectional view of a portion of a proximal portion of an elongate body member of the suturing device illustrating the fit between a spring and a push wire.
Figure 2F:
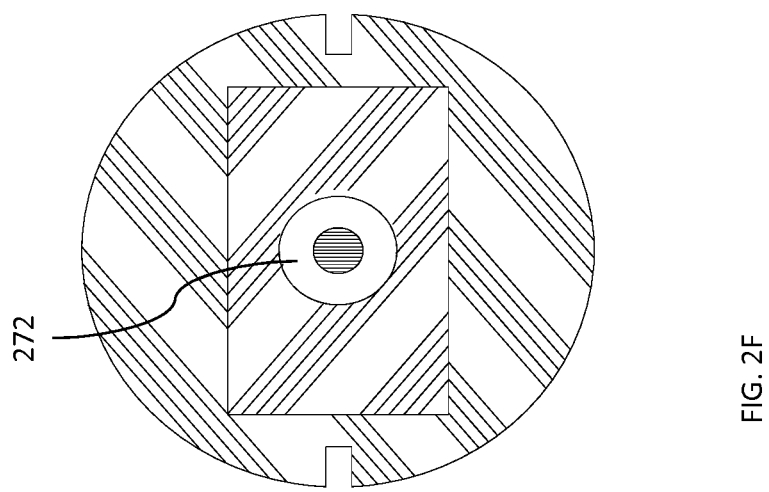
FIG. 2F is an enlarged cross-sectional view of a portion of a proximal portion of an elongate body member of the suturing device illustrating the fit between the push wire and a shaft.
Figure 2G:
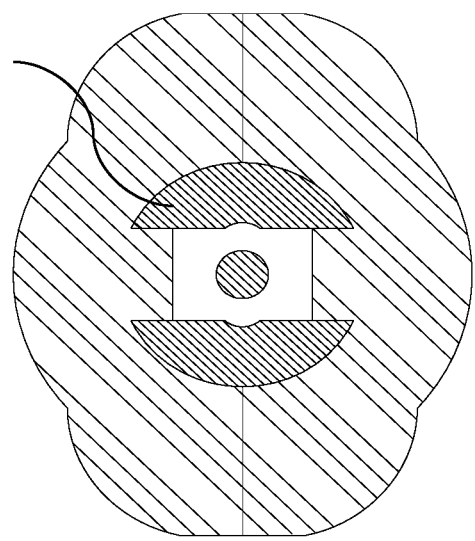
FIG. 2G is an enlarged cross-sectional view of a portion of a distal portion of the suturing device illustrating anti-rotation bosses.
Figure 2H:
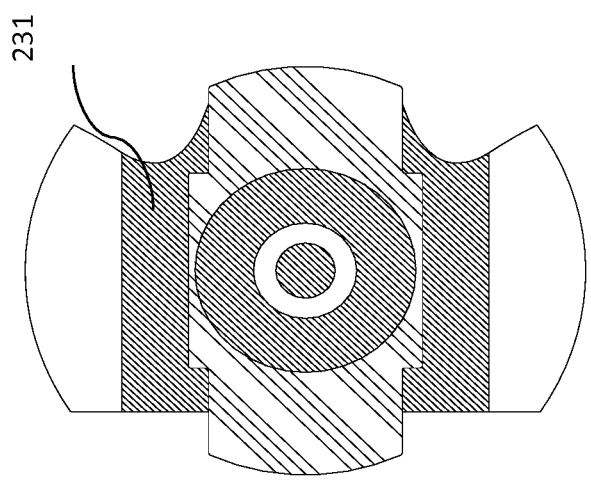
FIG. 2H is an enlarged cross-sectional view of a portion of a distal portion of the suturing device illustrating grinds for anti rotation.
Figure 21:
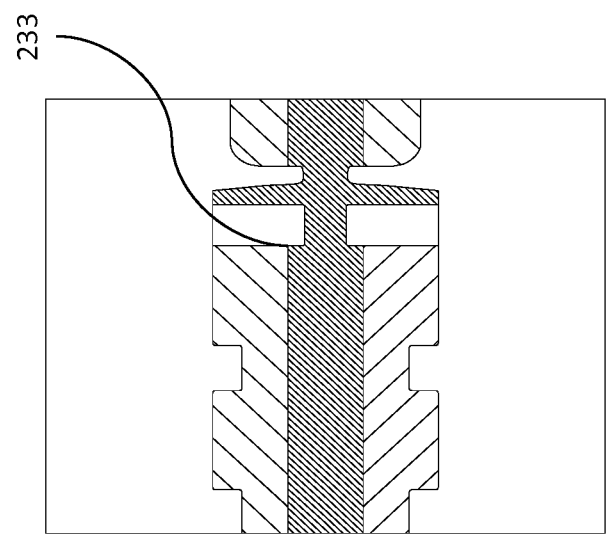
Figure 2J:
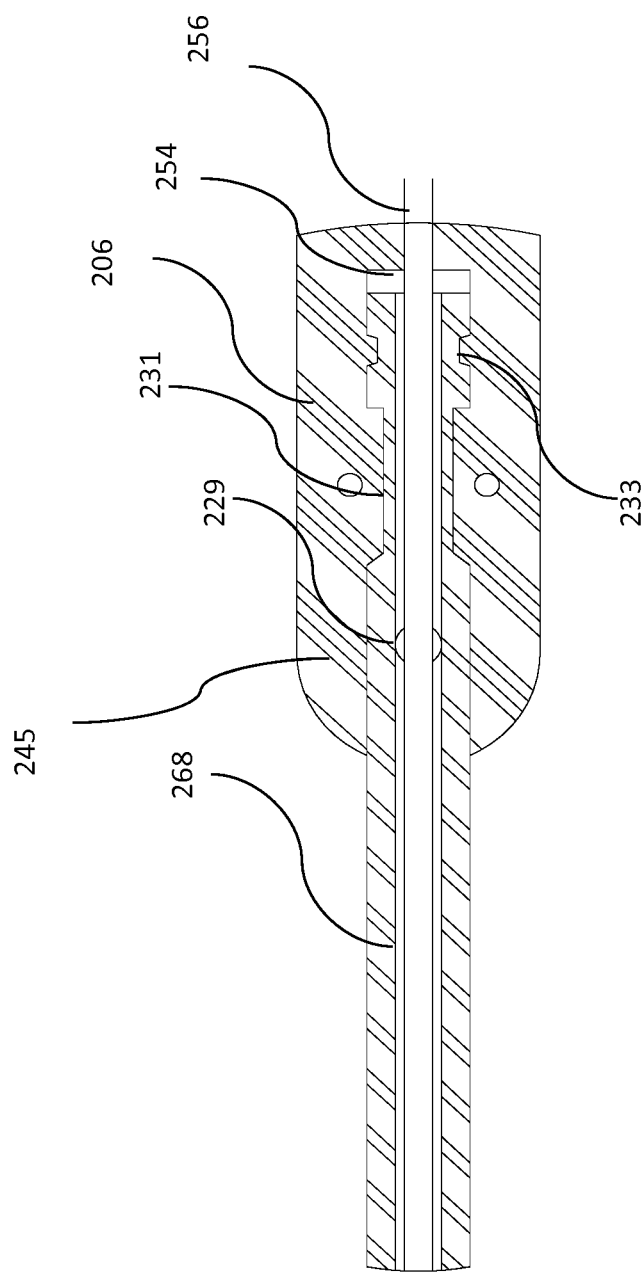
FIG. 2J is an enlarged cross-sectional view of a portion of a distal portion of the suturing device illustrating a fit between a wire assembly and a washer.

The bearing 224 connects the handle 222 to the spring tube 250 of the actuator 244 by way of a handle clearance 258 (as illustrated in FIG. 2D) provided at a proximal end portion 260 of the spring tube 250. In some embodiments of the invention, the spring tube 250 may be flanged for strength. The spring 248 encircles the spring tube 250 and abuts the handle 222 end. The spring 248 is compressed between the handle 222 end and a spring washer 262. The spring washer 262 abuts the end of the spring tube 250 and is seated upon a center tube 264. In some embodiments, the center tube 264 is hollow and housed by a portion of the spring tube 250. The center tube 264 forms a second cylindrical surface 266 to the push-wire 256. The push-wire 256 is coupled to the spring tube 250 by way of a weld, a coupling adhesive or other means, and is slidably disposed within a cannula 268. The cannula 268 is coupled to the spring tube 250 by snap-fit mechanism as shown in FIG. 2E. The cannula 268 is disposed within the second cylindrical surface 266. In one embodiment, the push-wire 256 is constructed of Nitinol (nickel-titanium alloy), so chosen for its combination of properties that allow for flexibility and high column strength when constrained. A distal end 270 of the center tube 264 provides for a shaft clearance 272 as shown in FIG. 2F. The shaft clearance 272 provides for the cannula 268 to be coupled to the shaft 252. The shaft 252 is configured to provide a passageway 274 to the cannula 268. In an exemplary embodiment of the invention, the shaft 252 can be insert molded or machined. The cannula 268 carrying the push-wire 256 runs across the shaft 252 and stops on a backstop washer 254 as shown in FIG. 2J. The push-wire 256 exits the cannula 268 at the backstop washer 254 and here it is coupled to a coupling 278. The coupling 278 is coupled to a carrier wire 280 thereby connecting the push-wire 256 and the carrier wire 280. The carrier wire 280 is coupled to the needle carrier 246 of the needle deployment mechanism 234 of the suturing device 200.

FIG. 2B is schematic view of a portion of the suturing device 200 of FIG. 2A, in accordance with an embodiment of the invention.

Referring to the needle deployment mechanism 234 in conjunction with FIGS. 2A and 2B, the push-wire 256 is attached by welding or other means to the coupling 278, which is slidably disposed within a pathway 282. The coupling 278 is attached to the carrier wire 280, which by virtue of its attachment to the coupling 278 is also slidably disposed within the pathway 282. The carrier wire 280 is mechanically coupled to the needle carrier 246 by means of a weld, a coupling, adhesives, or other means. The coupling 278 abuts the backstop washer 254 that is slidably disposed about the push-wire 256 and is contained within a first pocket 284 that includes a back wall 286, against which the backstop washer 254 rests. The pathway 282 terminates distally in a second pocket 288 that includes a wall. A down-stop washer 292 is slidably disposed about the carrier wire 280 and constrained within the second pocket 288.

FIG. 2C is an enlarged cross sectional view of the distal portion 206 of the elongate body member 202 depicting structural details of the needle receiving portion 294 of the suturing device 200 and the needle carrier 246 of the needle deployment mechanism 234 of the suturing device 200.

Referring to FIG. 2C, the structural components of the distal portion 206 of the elongate body member 202 of the suturing device 200 are elaborated in accordance with an embodiment of the invention.

As explained above, the needle carrier 246 is mechanically connected to the carrier wire 280 and is disposed within the lumen 226 of the elongate body member 202 in the curved portion 212. A distal portion 296 of the needle carrier 246 defines a channel 298 for holding the needle 236. The curved portion 212 also defines the second opening 216 for receiving a tissue. The distal portion 206 of the elongate body member 202 may include a slot 201 configured to act as a loading point 203 for a suture 235 coupled to the needle 236 at a proximal end 237 (illustrated in FIG. 2S later separately) of the needle 236. In some embodiments, the slot 201 ends behind the channel 298 of the needle carrier 246 to create an overlap between the slot 201 and the channel 298 (illustrated in FIG. 2M in detail). This overlap facilitates the process of suture loading.

An operator then inserts the needle 236 directly into the needle carrier 246 through the channel 298. In some embodiment, the suture 235 may extend out of the slot 201.

In accordance with some embodiments, the needle 236 may include a tip 207 and a shaft 209 coupled to the tip 207, thereby forming a shoulder 211. The shoulder 211 is coupled to the suture 235. The needle 236 can be held into the channel 298 of the needle carrier 246 by frictional fit or some other coupling mechanism (these details illustrated in FIG. 2S).

In accordance with some embodiments of the invention, the channel 298 provided in the needle carrier 246 can be molded through metal injection molding techniques.

Figure 3C:
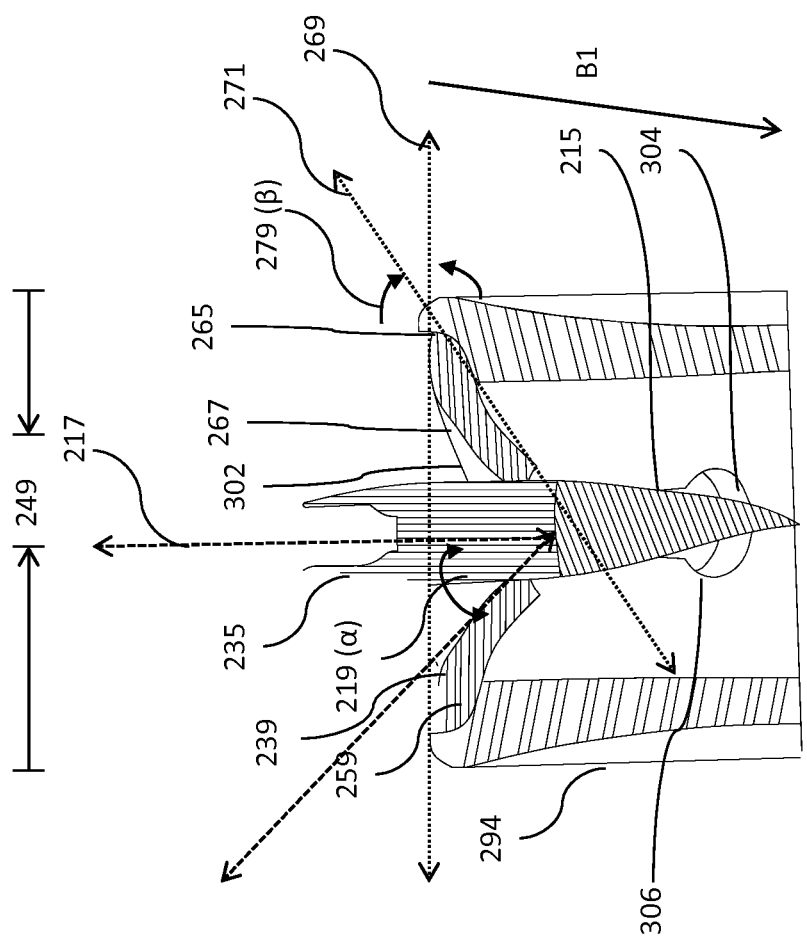
FIG. 3C is an enlarged cross-sectional view of a needle receiving portion of a suturing device, in accordance with an embodiment of the present invention.

Referring again to FIG. 2C, in accordance with some embodiments of the invention, the needle receiving portion 294 includes a non-planar surface 213 with walls 239 that converge to form an aperture 215 formed in the needle receiving portion 294 to receive the needle 236. The walls 239 of the needle receiving portion 294 are angled with respect to an axial direction 217 of the needle receiving portion 294 (or the direction in which a needle is received by the needle receiving portion) such that the walls 239 form an acute angle 219 (denoted by symbol 219 ($\alpha$) in FIG. 3C later) with the axial direction 217 of the needle receiving portion 294. Accordingly, the walls 239 of the needle receiving portion 294 are not parallel with the longitudinal axis of the needle receiving portion 294. For example, the angle may be 30 degree or 40 degree or any other angle as required for an appropriate procedure and needle alignment with the needle receiving portion 294. In some embodiments, the non-planar surface 213 can be a conical or a substantially conical surface (as illustrated in FIG. 3C). In some other embodiments, various other shapes may also be possible.

In some embodiments, the walls 239 of the non-planar surface 213 are angled with respect to the axial direction 217 (as shown in FIG. 3C) in such a manner that there is a gradual decrease in an aperture diameter 253 of the aperture 215 created by the non-planar surface 213. This is configured to receive the needle 236 in a gradual manner and avoid misalignment. For example, in case of the non-planar surface 213 the diameter of the hollow space created by the walls 239 of the conical or concave surface decreases gradually to form the aperture 215 formed at the bottom of the non-planar surface 213. Therefore, the needle 236 that is received within the aperture 215 through the non-planar surface 213 gradually moves downward toward the aperture 215 and reduces or avoids a chance of misalignment of the needle 236 with the aperture 215.

Figure 3D:
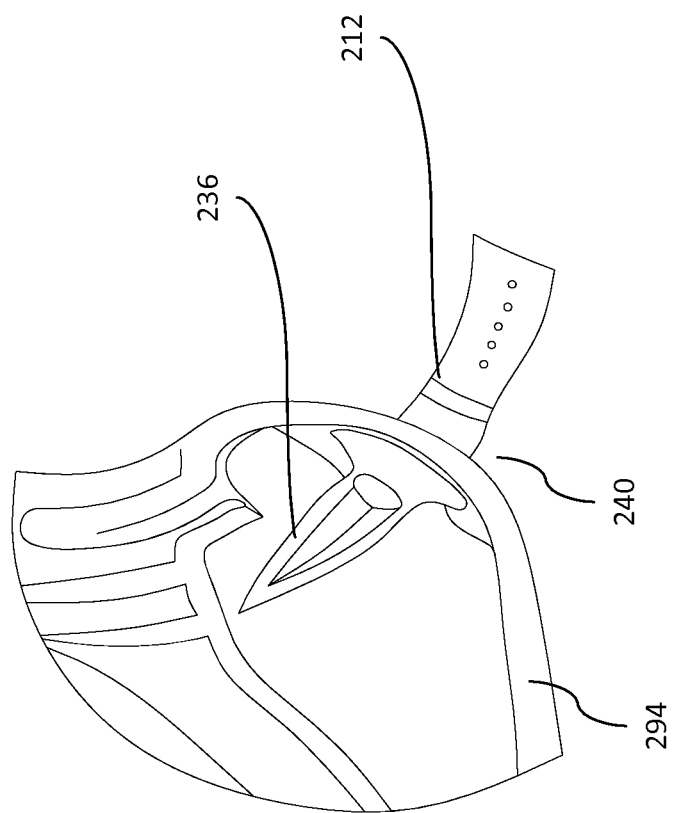
FIG. 3D is an enlarged view of a needle receiving portion of a suturing device in a deployed position, in accordance with an embodiment of the present invention.
Figure 3E:
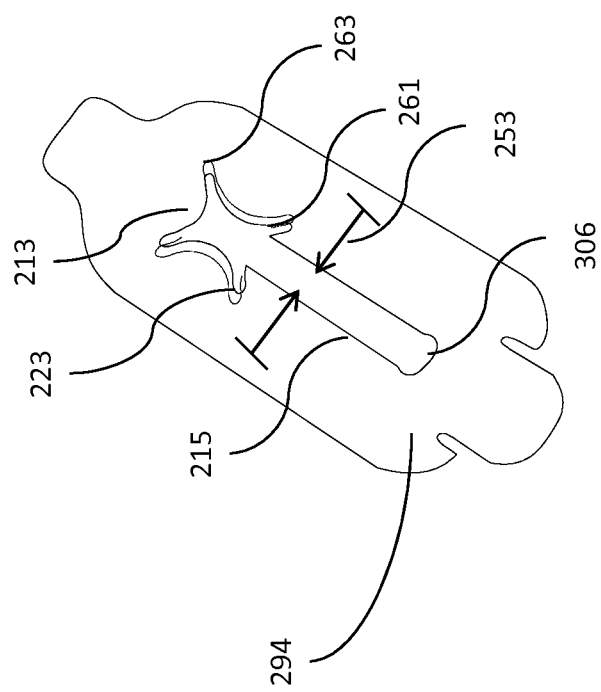
FIG. 3E is an enlarged view of radial slots provided in a needle receiving portion of a suturing device, in accordance with an embodiment of the present invention.

In some embodiments, the needle receiving portion 294 includes radial slots 223 provided on the walls 239 (shown in FIG. 3C) of the non-planar surface 213 of the needle receiving portion 294. The structure surrounding the radial slots 223 is configured to move from a first position 261 to a second position 263. In some embodiments, the first position is a position inside the needle receiving portion 294 proximal to an axis along the axial direction 217. In some embodiments, the second position is a position inside the needle receiving portion 294 distal to the axis (as illustrated in FIGS. 3C-3E). In accordance with these embodiments, there is an axial movement (expansion or compression) in the structure surrounding the radial slots that causes the radial slots to be in either the first position or the second position. The axial movement is defined by a movement toward or away from the axis. In still some other embodiments, there can be a lateral or side movement in the structure surrounding the radial slots that causes the radial slots 223 to be in either the first position 261 or the second position 263. The lateral movement is defined by a movement along sides while keeping axial distance from the axis constant.

In accordance with the embodiments of the invention, the needle receiving portion 294 has the non-planar surface 213. In some embodiments, the non-planar surface 213 has walls 239 that converge to provide an acute angle 219 ($\alpha$) to the aperture 215 with respect to the axial direction 217.

The movement of the structure surrounding the radial slots 223 allows the aperture 215 to open and allow entry of the needle 236 into the aperture 215 which can be referred to as the spring action. The spring action of the radial slots 223 may also be defined as moving of the walls 239 of the non-planar surface 213 from the first position 261 to the second position 263. The spring action of the radial slots 223 further facilitates closing of the aperture 215 after the needle 236 has entered the aperture 215. The closing of the aperture 215 allows capture of the needle 236 within the aperture 215. In accordance with other embodiments, the structure surrounding the aperture 215 provided in the needle receiving portion 294 can be made of a flexible material which is configured to flexibly open or close the aperture 215 based on a push or pull force exerted by the needle 236 on the aperture 215. In some other embodiments, the aperture 215 may also include a spring or any other resilient material which is configured to flexibly open or close the aperture 215.

In accordance with some embodiments, the needle receiving portion 294 includes a single aperture 215 configured to receive the needle 236. In other embodiments, the needle receiving portion 294 includes a plurality of apertures similar to the aperture 215. Each of the apertures, in such embodiments, may be associated with a non-planar surface such as the non-planar surface 213 (for example a conical surface) to ensure that receipt of needle 236 into any of the apertures will be preceded through a gradual entry along the non-planar surface 213. In some other embodiments, at least one of the apertures may be associated with the non-planar surface 213 such as the conical surface to ensure that receipt of needle 236 into the at least one of the apertures will be preceded through a gradual entry along the non-planar surface 213. Further, in such embodiments, the plurality of non-planar surfaces and the plurality of apertures may be provided adjacent to one another.

In some embodiments, the needle receiving portion 294 is configured to free float in the distal portion 206 by means of slip fitting the needle receiving portion 294 in grooves or slots within the distal portion 206. This may allow the needle receiving portion 294 to self-center on the distal portion 206 creating an assurance of needle catching. This is further explained in conjunction with FIG. 3C in detail.

Figure 6:
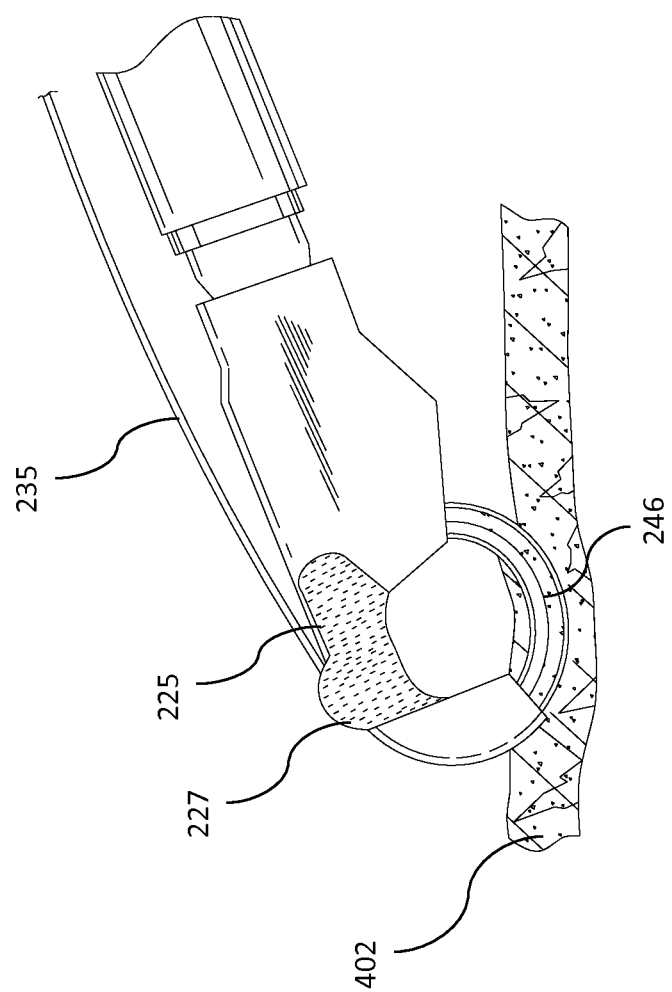
FIG. 6 illustrates an insertion depth controller, in accordance with an embodiment of the present invention.

In some embodiments of the invention, the needle receiving portion 294 includes a penetration depth controller 225 as illustrated in FIG. 6 to control penetration depth of the needle 236. The penetration depth controller 225 may include an adaptor 227 placed proximate to the needle carrier 246 at the distal portion 206 of the elongate body member 202 of the suturing device 200. The adaptor 227 may prevent the tissue from entering the second opening 216 by a defined limit, thus controlling the depth of bite of the needle carrier 246.

In accordance with some embodiments of the invention, the dimension of the inner diameter 230 of the elongate body member 202 is between 0.100 to 0.150 inches and the dimensional width of the needle receiving portion 294 is between 0.160-0.190 inches. This reduced size of the elongate body member 202 and that of the needle receiving portion 294 compacts the suturing device 200, in some embodiments of the invention.

In some embodiments, the suturing device 200 may include the anti-rotation mechanism 245. The anti-rotation mechanism 245 is disposed in the elongate body member 202 proximate to the distal portion 206 as illustrated in FIGS. 2A and 2B. The anti-rotation mechanism 245 facilitates positioning of the distal portion 206 of the suturing device 200 and prevents the distal portion 206 from rotating and falling off from the elongate body member 202. The anti-rotational mechanism is illustrated in FIGS. 2G-2I. FIG. 2J illustrates relative positions of different parts of anti-rotation mechanism 245 as present in the distal portion 206.

FIG. 2G illustrates anti-rotation bosses 229. The anti-rotation bosses 229 are placed in the distal portion 206 of the elongate body member 202. The anti-rotation bosses 229 are configured to prevent the distal portion 206 to tear away from the rest of the elongate body member 202. When the suturing device 200 is operated, the distal portion 206 is inserted into the body of the patient and so there is a chance that the distal portion 206 may tear off from the suturing device 200 and can be left inside the body of the patient. The anti-rotation bosses 229 are used to prevent the distal portion 206 from rotating as a result of the force applied by the operator on the suturing device 200, and thus avoid tearing off of the distal portion 206 from the suturing device 200.

FIG. 2H illustrates flat grinds 231 for anti-rotation placed proximate to the anti-rotation bosses 229 from FIG. 2G. The flat grinds 231 are configured to prevent the distal portion 206 from tearing away from the rest of the elongate body member 202. When the suturing device 200 is operated, the distal portion 206 is inserted into the body of the patient and so there is a chance that the distal portion 206 may tear off from the suturing device 200 and can be left inside the body of the patient. The flat grinds 231 are used to prevent the distal portion 206 from rotating as a result of the force applied by the operator on the suturing device 200, and thus avoid tearing off of the distal portion 206 from the suturing device 200.

FIG. 2I illustrates a 360 degree rotation ring 233 provided proximate to the flat grinds 231 from FIG. 2H. The 360 degree rotation ring 233 is configured to maintain the position of the distal portion 206 of the elongate body member 202 in case the anti-rotation bosses 229 and/or the flat grinds 231 fail to prevent rotation of the distal portion 206 of the elongate body member 202 of the suturing device 200.

FIG. 2J illustrates an enlarged cross sectional view of a portion of the distal portion 206 of the suturing device 200. In some embodiments of the invention, the cannula 268 housing the push-wire 256 abuts the backstop washer 254. The mechanism has been described in detail in conjunction with FIG. 2B.

Figure 2K:
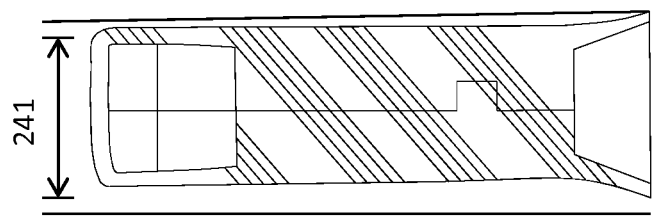
FIG. 2K is an enlarged cross-sectional view of a portion of a distal portion of the suturing device illustrating width of a distal portion of the suturing device.

In accordance with an embodiment of the invention as illustrated in FIG. 2K, a width 241 of the distal portion 206 of the elongate body member 202 at the thickest portion may vary from 0.215 inches to 0.220 inches. The width 241 may facilitate in less dissection while using the suturing device 200. However, in certain other embodiment the width dimension may vary based on requirements.

Figure 2L:
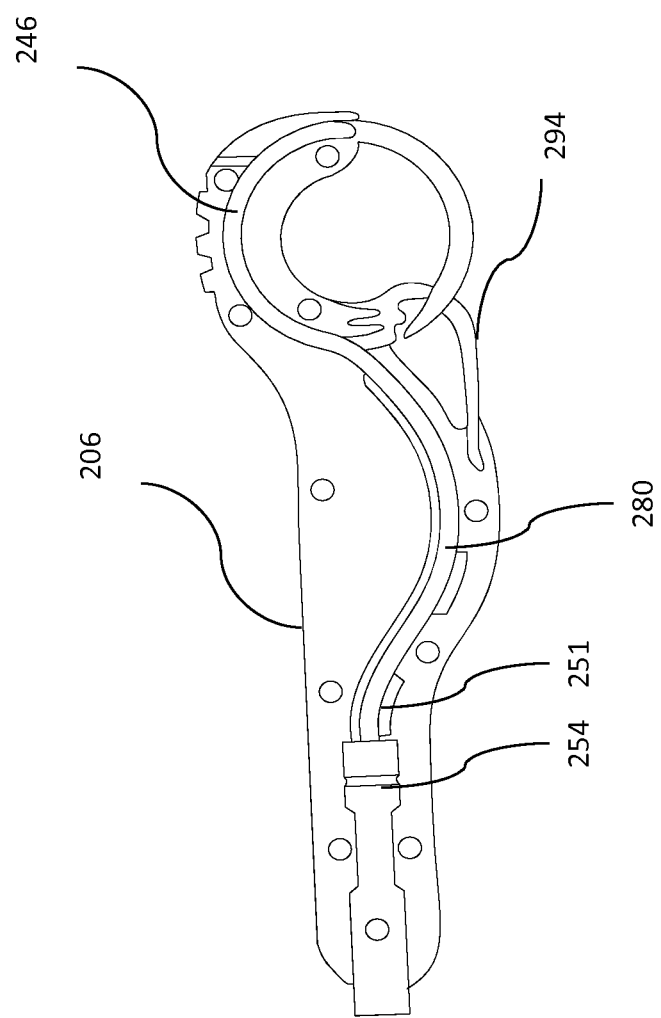
FIG. 2L is an enlarged view of a distal portion of the suturing device.

FIG. 2L illustrates embossments 251 provided around the carrier wire 280. The embossments 251 are provided at the distal portion 206 of the elongate body member 202 proximate to the channel 298 provided in the needle carrier 246. In some embodiments of the invention, the embossments 251 are provided along the carrier wire 280 to aid in wire assembling.

Figure 2M:
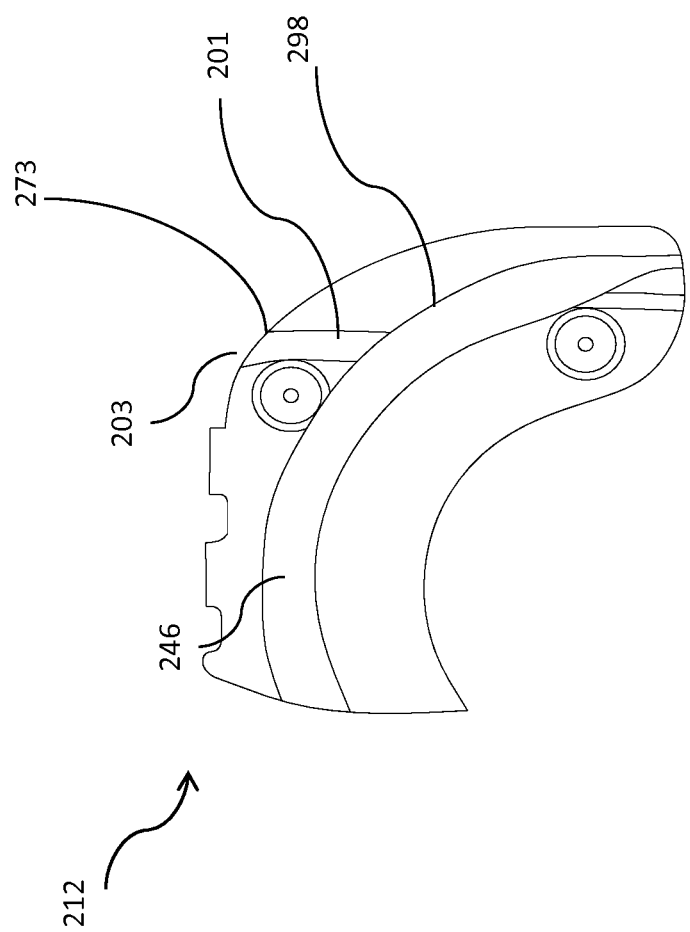
FIG. 2M is an enlarged view of a distal portion of the suturing device illustrating the receiving portion.

FIG. 2M illustrates the curved portion 212 of the distal portion 206 of the elongate body member 202. The curved portion 212 has been described above.

Figure 2N:
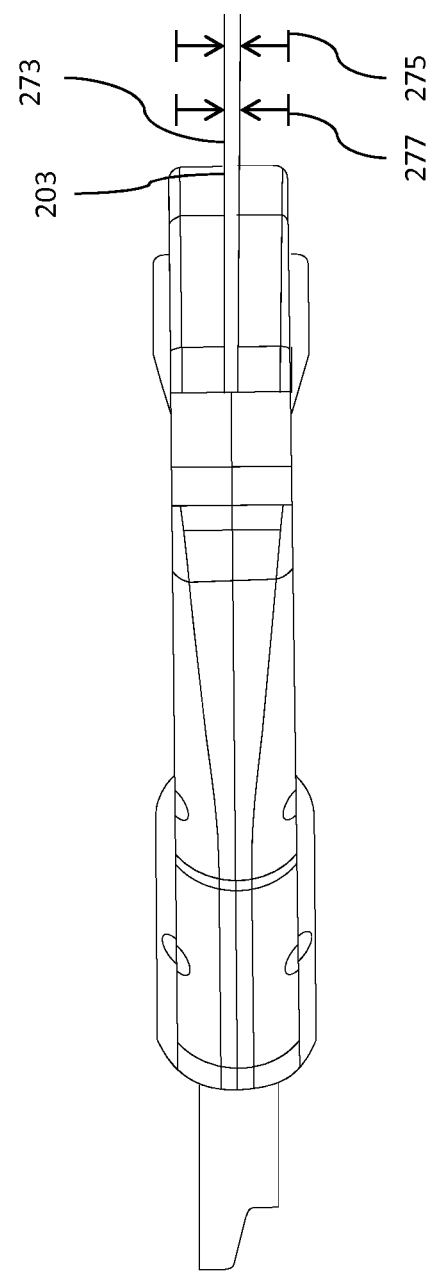
FIG. 2N is an enlarged view of a distal portion of the suturing device.
Figure 20:
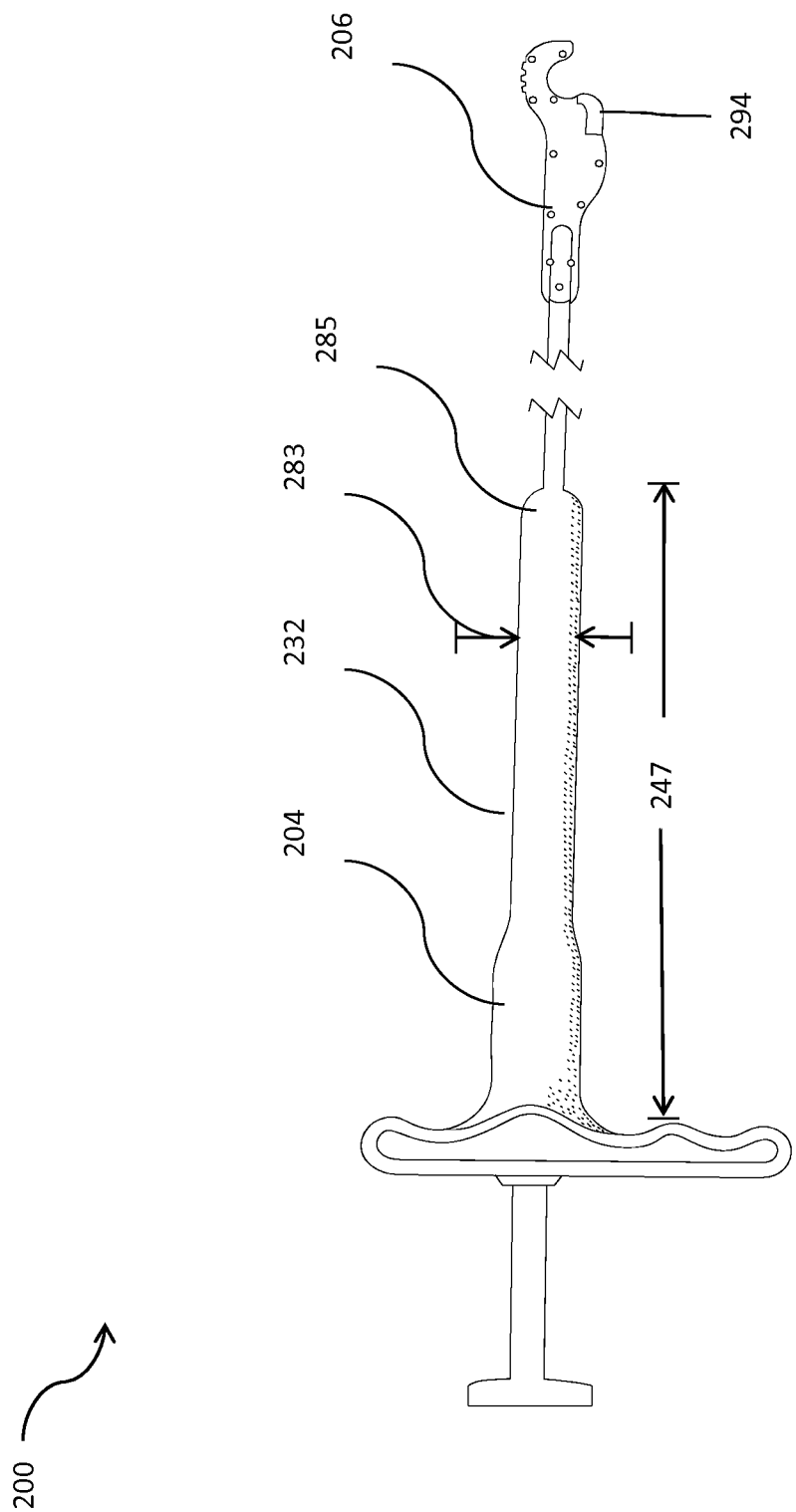

FIG. 2N illustrates a top view of the distal portion 206 of the elongate body member 202 of the suturing device 200. FIG. 2N illustrates the loading point 203 that is configured for loading the suture 235 onto the suturing device 200. The loading point 203 defines a tapered end 273. The tapered end 273 offers a tapered entry to the suture 235. In some embodiments, the loading point 203 is continued into the slot 201. In some embodiments, the slot 201 overlaps with the channel 298 of the needle carrier 246 when the suturing device 200 is in the retracted position 238. The tapered end 273 accepts the suture 235 and guides it into the slot 201 through the loading point 203 when the needle 236 and the suture 235 are loaded onto the suturing device 200.

In some embodiments, the tapered end 273 defines a first width 275 and a second width 277 such that the first width 275 and the second width 277 have different dimensions. In some embodiments, the dimension of the first width 275 is greater than the dimension of the second width 277. The dimension of the first width 275 can vary based on requirements. In an exemplary embodiment, the first width 275 can vary between 0.500 mm to 0.510 mm. The dimension of the second width 277 can also vary based on requirements. In an exemplary embodiment, the second width 277 can vary between 0.330 mm to 0.355 mm.

In accordance with some embodiments of the invention, the suturing device 200 is housed in a tubing shrink 232 as illustrated in FIG. 2O. In some embodiments of the invention, the tubing shrink 232 provides a housing for the proximal portion 204 of the elongate body member 202 of the suturing device 200.

Figure 2P:
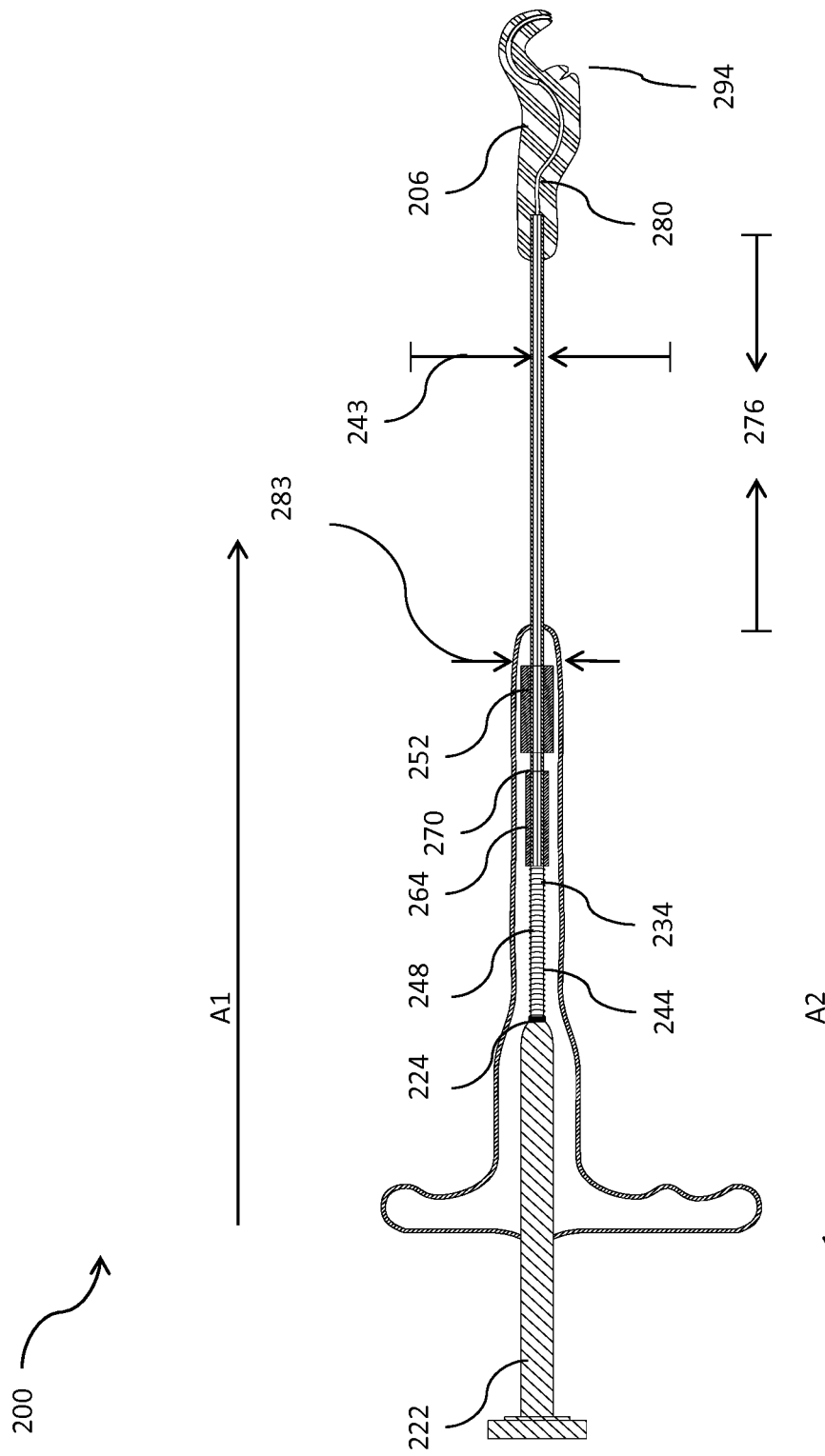
FIG. 2P illustrates a working length of a suturing device.

Referring to FIGS. 2P and 2Q, wherein the retracted position 238 and the deployed position 240 are illustrated respectively. FIG. 2P illustrates a working length 276 of the suturing device 200 is illustrated. In some embodiments of the invention, the working length 276 is a part of the length 208 of the elongate body member 202. In some embodiments of the invention, the working length 276 may vary between 90 mm to 110 mm (approximately 3.54 inches-4.00 inches). In some embodiments of the invention, the thickness 243 of the elongate body member 202 along the working length 276 of the elongate body member 202 of the suturing device 200 may vary between 0.110 inches to 0.130 inches. This contributes to a downsized profile of the device thereby enabling the physicians to place their fingers alongside the device during placement and allows for less dissection requirement. This may make the device minimally invasive in nature. In some embodiments of the invention, the working length 276 abuts the end of the tubing shrink 232. In an exemplary embodiment of the invention, the working length 276 of the suturing device 200 is housed in the tubing shrink 232 as illustrated in FIG. 2P.

In some embodiments of the invention, the tubing shrink 232 abuts the end of the working length 276 of the suturing device 200. In some embodiments of the invention, the length 247 of the tubing shrink 232 may vary from 5 inches to 6 inches. In an exemplary embodiment of the invention, the length 247 of the tubing shrink 232 can be 5.5 inches. In an exemplary embodiment of the invention, the tubing shrink 232 can be made of polyolefin.

In some embodiments, the tubing shrink 232 of the suturing device 200 defines a width 283. The width 283 can vary based on requirements and can also vary along the length 247 of the tubing shrink 232. For example, in some embodiments, the width 283 can be around 20 mm in the proximal portion 204 of the elongate body member 202 and it can be around 11 mm around an end portion 285 of the tubing shrink 247.

Figure 2R:
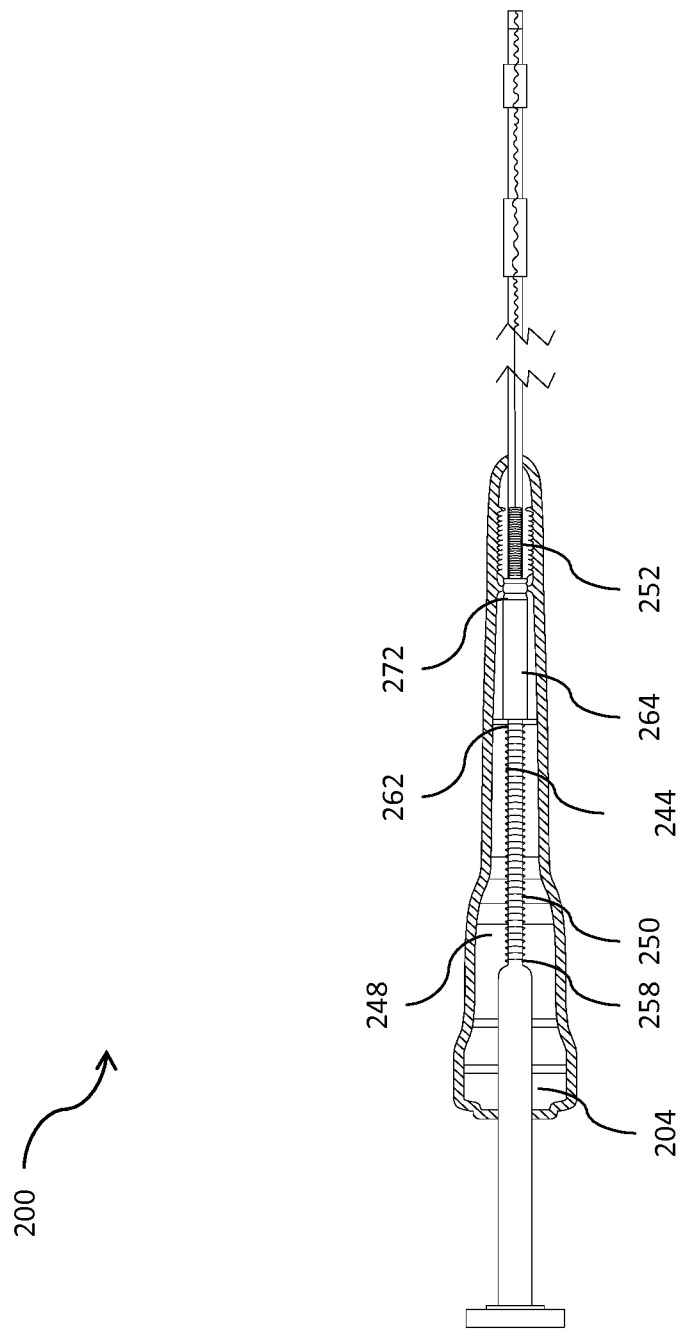
FIG. 2R is a cross-sectional front view of a portion of an elongate body member.

FIG. 2R is a cross sectional view of the proximal portion 204 of the elongate body member 202. The mechanism of operation and construction of the proximal portion 204 of the elongate body member 202 has been described earlier. FIG. 2R illustrates the positions of the handle clearance 258, the shaft clearance 272, as described in conjunction with some embodiments of the invention above.

FIG. 2S illustrates the needle 236 as present in some embodiments of the invention.

Having described the suturing device 200 above, an overview of the structural cooperation between various portions or elements of the suturing device 200 is provided below.

In a general aspect, at least a portion of the elongate body member 202 of the suturing device 200 coupled to the suture 235 is inserted into a body of a patient. In some embodiments, the needle carrier 246 of the needle deployment mechanism 234 can be configured to slidably move through the lumen 226 and configured to hold the needle 236, thereby slidably moving the needle 236 into the lumen 226 of the elongate body member 202, in the retracted position 238. The needle carrier 246 is further configured to move into at least a portion of the needle receiving portion 294 along with the needle 236 in the deployed position 240. The needle carrier 246 that is slidably disposed along the lumen 226 of the elongate body member 202 in the refracted position 238 can be actuated such that the needle 236 moves through a bodily tissue into the body of the patient.

In some embodiments, the actuator 244 is configured to actuate the suturing device 200 to the deployed position 240 from the retracted position 238. The actuator 244 moves the needle 236 along the direction A1 and back to the retracted position 238 from the deployed position 240 by moving the needle 236 along the direction A2.

In some embodiments, actuating can include moving the suturing device 200 in the direction A1. The needle 236 can be moved slidably into the lumen 226 in the direction A1 along the lumen 226 and away from the proximal portion 110 of the elongate body member 202, and toward the needle receiving portion 294 of the suturing device 200 until the needle 236 has moved into the non-planar surface 213. In some embodiments, the suture 235 is loaded in the distal portion 206 of the elongate body member 202. The distal portion 206 defines the opening 214 through which the needle 236 comes out of the lumen 226 when the suturing device 200 is actuated along the direction A1. In some embodiments, the aperture acts as a capture slot for the needle 236 when it moves toward the needle receiving portion 294 on being actuated along the direction A1.

In some embodiments, the suturing device 200 is placed such that the bodily tissue (to be suture 235) is present between the distal portion 206 of the elongate body member 202 of the suturing device 200 and the needle receiving portion 294 of the suturing device 200. When the needle 236 is actuated along direction A1, it passes through the second opening 216 (where the bodily tissue is placed) and moves toward the aperture 215 of the needle receiving portion 294. When the needle 236 enters the needle receiving portion 294, it is received by the aperture 215 in the non-planar surface 213 of the needle receiving portion 294. The radial slots 223 along the walls 239 of the non-planar surface 213 move from the first position 261 to the second position 263 (illustrated later in FIG. 3E) as a result of a push force exerted by the needle 236 onto the walls 236 of the non-planar surface 213.

In some embodiments, when the walls 239 surrounding the radial slots 223 move to the second position 263, a space is created for the needle 236 to enter the aperture. In some embodiments, the needle 236 can have a dimension greater than the aperture diameter 253. When the needle 236 enters the aperture 215, the radial slots 223 move back to the first position 261, thereby capturing the needle 236 into the aperture 215. The suture 235 that is coupled to the needle 236 is thereby effectively passed through the bodily tissue (the suture 235 is coupled to the needle 236; therefore it will pass through the bodily tissue along with the needle 236). When the needle 236 is captured into the aperture 215 of the needle receiving portion 294, the suture 235 is effectively passed through the tissue. In some embodiments, the radial slots 223 define a space. In other words, there is a space between the sidewalls of adjacent non-planar surfaces 213. In some embodiments, the sidewalls of adjacent non-planer surfaces 213 contact each other to define the radial slots 223. In some embodiments, the non-planar surfaces 213 include a linear or planar portion. In other embodiments the non-planar surfaces 213 include a convex or a concave portion.

In some embodiments, actuating can include moving the suturing device 200 in the direction A2. The needle 236 can be moved slidably into the lumen 226 in the direction A2 along the lumen 226 and toward the proximal portion 204 of the elongate body member 202, and away from the needle receiving portion 294 of the suturing device 200 until the needle carrier 246 has moved out of the non-planar surface 213. In some embodiments, the actuator 244 as discussed above can be configured to move the suturing device 200 back and forth along the direction A1 and A2. FIG. 3A to FIG. 3F illustrate various enlarged cross sectional views of the needle receiving portion 294, in accordance with some embodiments of the present invention. In some embodiments, the needle receiving portion 294 may define a linear opening. In other embodiments, the needle receiving portion 294 defines a circular opening or a different shaped opening.

Referring to FIG. 3A and FIG. 3B in conjunction with FIGS. 2A-2C, a mechanism of action of the suturing device 200 is described. The retracted position 238 and deployed position 240 of the actuator 244 of the needle deployment mechanism 234 are shown in FIG. 3A and FIG. 3B respectively.

In operation, an operator as described above actuates the needle deployment mechanism 234 by pushing on the handle 222, which via the attachment to the spring tube 250 which is attached to the push-wire 256, moves the coupling 278 along the pathway 282 concomitantly moving the carrier wire 280, which slidably moves the needle carrier 246 through the opening 214. The user continues to push the handle 222 until the needle 236 enters the needle receiving portion 294. The needle receiving portion 294 has the non-planar surface 213 to guide the needle 236 into the aperture 215. The aperture 215 in the needle receiving portion 294 captures the needle 236 into the aperture 215.

Referring to FIGS. 3C-3E in conjunction with FIGS. 2A-2C, the non-planar surface 213 and the aperture 215 of the needle receiving portion 294 are described.

The needle receiving portion 294, as shown in FIG. 3C, defines an opening 302 defined by the non-planar surface 213. The needle receiving portion 294 receives the needle 236 coupled to the suture 235 by means of the needle 236 through the opening 302. The non-planar surface 213 guides the needle 236 to pass through the opening 302. The opening 302 culminates into the aperture 215. The aperture 215 is lined with the radial slots 223 along the walls 239. The radial slots 223 create a spring mechanism and allow the aperture 215 to open to allow the entry of the needle 236 into the aperture 215. The spring action of the radial slots 223 may be defined as moving of the walls 239 of the non-planar surface 213 from the first position 261 to the second position 263 (illustrated in FIG. 3E). After the needle 236 has passed the opening 214 and the opening 216, and has entered the aperture 215, the radial slots 223 spring back to their original position defining the aperture 215, and the needle 236 remains captured in the needle receiving portion 294. The user releases the handle 222 and the spring 248 urges the handle 222 proximally, moving the push-wire 256, the coupling 278, the carrier wire 280, and the needle carrier 246 proximally along with the handle 222 to the retracted position 238. When it is necessary to remove the needle 236 from the needle receiving portion 294, the needle 236 may be moved toward an enlarged portion 304. The enlarged portion 304 is sized to allow the needle 236 to pass through without resistance.

In some embodiments, the needle receiving portion 294 is formed using die stamping technique, where the die is cast out of a flat sheet of metal. In some embodiments, the metal used for die stamping can be stainless steel which can be chosen from any of 455 custom stainless steel, 301 stainless steel, 302 stainless steel, 303 stainless steel. The needle receiving portion 294 is provided with the non-planar surface 213 and would therefore make allowance for the suturing device 200 and avoid misalignment due to tissue entering the needle receiving portion 294.

In present embodiment of the invention, the needle receiving portion 294 is designed to receive a single needle such as the needle 236 at a given time so as to make allowance for the device misalignment caused by needle 236 hitting the land area.

In some embodiments of the invention, the non-planar surface 213 is defined by a width 249. The width 249 can vary based on requirements. In some exemplary embodiments, the width 249 of the non-planar surface 213 may vary between 0.170 inches to 0.180 inches. This may provide a greater non-planar area and therefore more assurance for needle capture.

In some embodiments, the non-planar surface 213 contains a top edge 265 and an angled side edge 267. The angled side edge 267 is present on both lateral sides of the non-planar surface 213. In some embodiments, the top edge 265 runs along a plane 269 and the angled side edge 267 runs along a plane 271 such that an acute angle 279 ($\beta$) is formed between the top edge 265 and the angled side edge 267. In some embodiments, the angled side edge 267 is provided on the walls 239 of the non-planar surface 213. The convergence of the angled side edge 267 provides for the gradual decrease in the aperture diameter 253 of the aperture 215.

In some embodiments, the angled side edge 267 on both lateral sides of the non-planar surface 213 converge along a direction B1 and form the aperture 215. In some embodiments, the aperture 215 also forms an acute angle 219 ($\alpha$) with the angled side edge 267 (or with the walls 239 of the non-planar surface 213).

In some embodiments, the radial slots 223 are present along the angled side edge 267 lined on the walls 239 of the non-planar surface 213. In some embodiments, the radial slots 223 are configured to move from the first position 261 to the second position 263 thereby increasing the aperture diameter 253 and allowing for the needle 236 to enter the aperture 215.

In some embodiments, the aperture 215 defines a distal end 306 of the aperture 215 which provides for the enlarged portion 304.

In some embodiments, the non-planar surface 213 is provided with a free float mechanism 259 (illustrated in FIG. 3C). The free float mechanism 259 enables the non-planar surface 213 to slide back and forth on both sides of the non-planar surface 213. In some embodiments, the needle receiving portion 294 is configured to free float in the distal portion 206 of the elongate body member 202 by means of slip fitting the needle receiving portion 294 in grooves or slots within the distal portion 206. This may allow the needle receiving portion 294 to self-center on the distal portion 206 creating an assurance of needle catching. In some embodiments, the non-planar surface 213 of the needle receiving portion 294 is configured to slide laterally on both sides of the needle receiving portion 294.

In some embodiments, an empty space may be provided between outer surfaces of the non-planar surface and surrounding portion of the needle receiving portion such that the non-planar surface is mobile with respect to the surrounding structure or portion of the needle receiving portion. In some embodiments, the width of the empty space along a horizontal plane may vary based on requirements. In some exemplary embodiments, this width can vary between 0.00254 mm to 0.00170 mm on either side of the non-planar surface 213 laterally.

Referring to FIG. 3D in conjunction with FIGS. 2A-2C in accordance with an embodiment of the invention, needle entry into the needle receiving portion 294 is illustrated, wherein the actuator 244 of the needle receiving portion 294 of the suturing device 200 is shown in the deployed position 240. As has been illustrated by the way of FIG. 3D, the suturing device 200 does not have a blunt surface thereby preventing any bodily tissues to get struck inside the needle receiving portion 294 which may prevent any misalignment of the suturing device 200 caused due to bodily tissues entering the needle receiving portion 294.

Referring to FIG. 3E in conjunction with FIGS. 2A-2C in accordance with the present embodiment of the invention, a cross sectional view of the radial slots 223 is illustrated. The radial slots 223 allow the aperture 215 to spring open and capture the needle 236 into the needle receiving portion 294 of the suturing device 200.

Figure 3F:
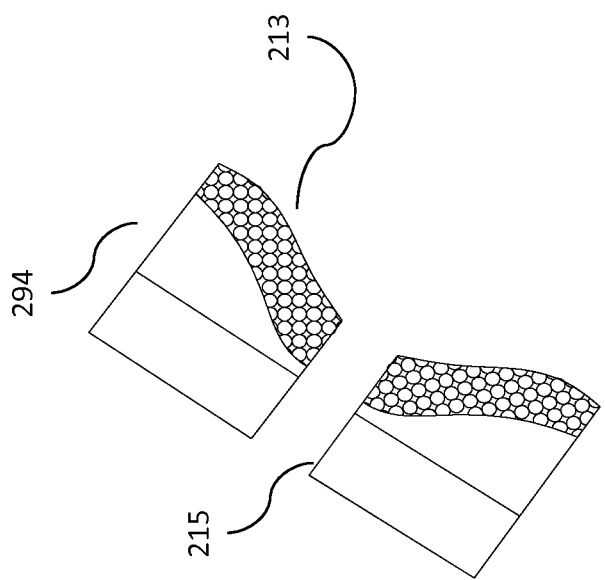
FIG. 3F is a cross sectional view of a non-planar surface of a needle receiving portion of a suturing device, in accordance with an embodiment of the present invention.

Referring to FIG. 3F in conjunction with FIGS. 2A-2C in accordance with an embodiment of the invention, the non-planar surface 213 of the needle receiving portion 294 of the suturing device 200 is illustrated. The non-planar surface 213 guides the needle 236 into the aperture 215 by the way of walls 239 that are angled with respect to the top edge 265 of the non-planar surface 213.

Figure 3G:
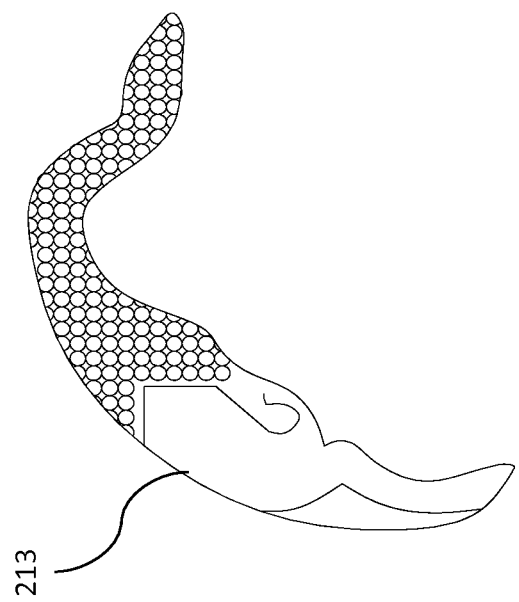
FIG. 3G illustrates a cross sectional view of a non-planar surface of a needle receiving portion of a suturing device, in accordance with an embodiment of the present invention.

Referring to FIG. 3G in conjunction with FIGS. 2A-2C in accordance with an embodiment of the invention, the non-planar surface 213 of the needle receiving portion 294 of the suturing device 200 is illustrated. In some embodiments, the needle receiving portion 294 can be made of a flexible material that is configured to flexibly open or close the aperture 215 based on a push or pull force exerted by the needle 236 on the aperture 215.

In some embodiments of the invention, the needle receiving portion 294 is made up of 303 full hard stainless steel. Other materials that can be used to improve the capture performance include, Nitinol, or a 400 series heat treatable stainless material.

In accordance with some embodiments of the invention, there are four radial slots 223. This number can be reduced to two to maximize area of the non-planar surface 213 or the radial slots 223 can increased to six to create a more easily deflected spring mechanism.

In some embodiments of the invention, the number of radial slots 223 around the aperture 215 can be minimized or maximized in order to design the needle receiving portion 294 to capture various needle geometries.

Figure 3H:
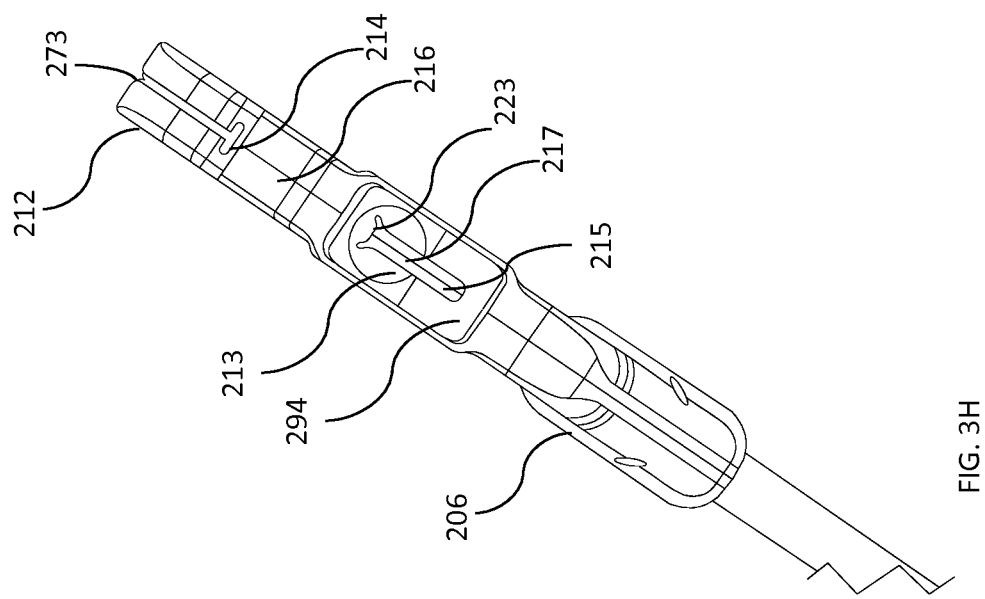
FIG. 3H illustrates a side view of a needle receiving portion and a distal portion of an elongate body member of a suturing device, in an embodiment of the present invention

In some embodiments of the invention, the number of the radial slots 223 can be reduced to two to maximize the area of non-planar surface 213 for a better interface for the needle 236. In accordance with various other embodiments, the number of radial slots 223 can vary based on the requirements. FIG. 3H illustrates a lateral view of the needle receiving portion 294 along with the distal portion 206.

Figure 4A:
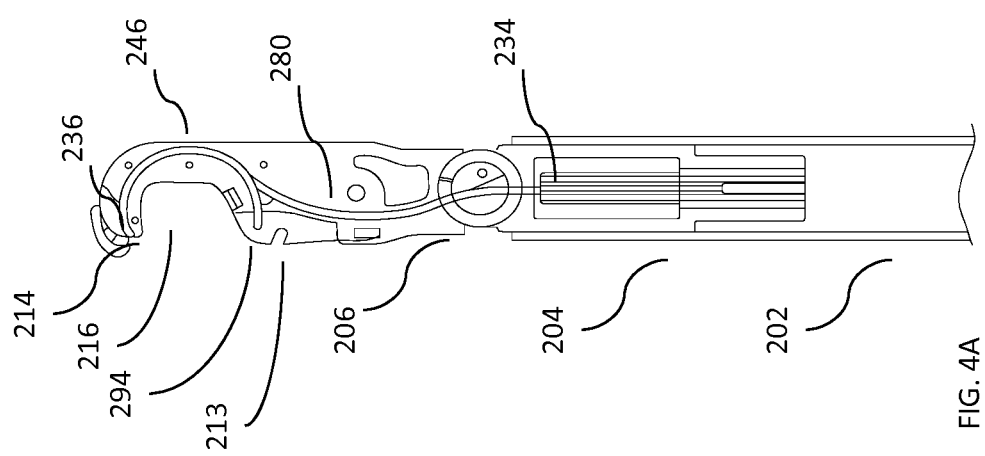
FIGS. 4A-4C illustrate a mechanism of operation of a suturing device, in accordance with an embodiment of the present invention.
Figure 4B:
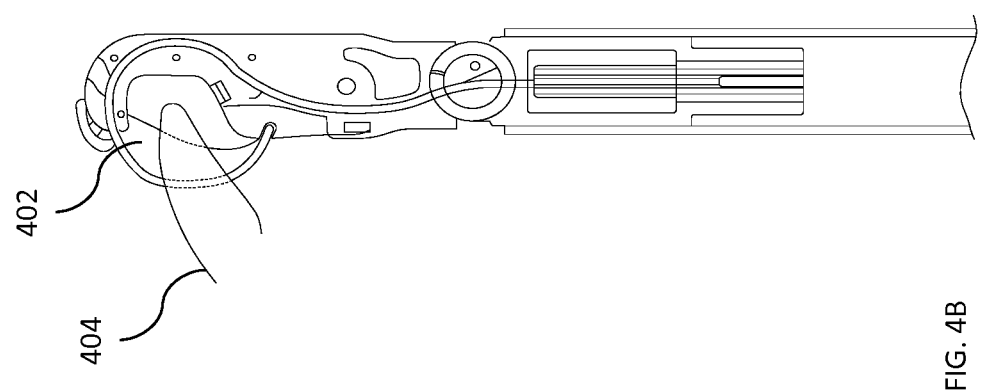
Figure 4C:
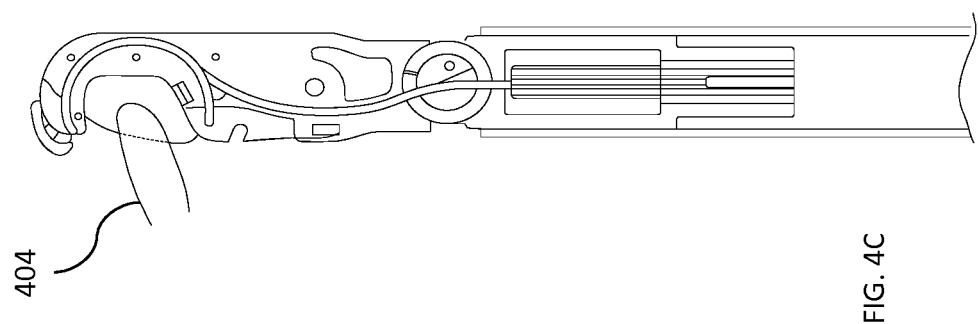

FIGS. 4A-4C illustrate a method of operation of the suturing device 200.

Referring now to FIGS. 4A-4C in conjunction with FIGS. 2A-2C, the method of operation of the suturing device 200 is described in accordance with an embodiment, of the present invention. The suturing device 200 is used for suture 235 placement inside body tissues, for example in a pelvic region of a patient. In some embodiments, the suturing device 200 is employed during the treatment of genital prolapse. The suturing device 200 may be used by the operator as defined above. In some embodiments, the operator can load the suture 235 through the loading point 203.

In some embodiments, the suture 235 can be pulled by attaching the suture 235 to a spool (not shown) mounted on the elongate body member 202 of the suturing device 200. The operator can then insert the elongate body member 202 into a patient body and orient the elongate body member 202 so that the opening 214 is proximate to or in contact with a bodily tissue 402 to be sutured. In some embodiments, the bodily tissue 402 (shown in FIG. 4B) is a first portion of a pelvic tissue (as described later in FIG. 5). The operator can then push the handle 222 (shown in FIG. 2A), as described above. Pushing the handle 222 causes the needle carrier 246 holding the needle 236 to extend out of the opening 214 and push the needle 236 through the tissue 402. As the needle 236 is pushed through the tissue 402, the needle 236 pulls a first suture 404 through the tissue 402. As the operator continues to push the handle 222, the needle carrier 246 continues to advance out of the opening 214 and directs the needle 236 and the first suture 404 toward the needle receiving portion 294 provided at the distal portion 206 of the elongate body member 202 of the suturing device 200. The operator continues to push the handle 222 until the needle 236 contacts and becomes captured by the needle receiving portion 294 as explained by the way of FIG. 4B. The needle receiving portion 294 of the suturing device 200 guides the needle 236 into the aperture 215 by means of the non-planar surface 213. In some embodiments, the aperture 215 has walls 239 hinged by radial slots 223 that allow the aperture 215 to open to allow entry of the needle 236 and then close to capture the needle 236 within the aperture 215. The operator then retracts the needle carrier 246 by releasing the handle 222 and bringing the actuator 244 to the retracted position 238, as previously described.

After the operator releases the handle 222, the actuator 244 comes into its retracted position 238 and the needle 236 and the first suture 404 are left captured within the needle receiving portion 294, with the first suture 404 extending through the tissue 402 (shown in FIG. 4C). When the actuator 244 returns to the retracted position 238, the operator pulls out the suturing device 200 from the patient's body leaving the first suture 404 placed into the patient's body.

Figure 5:
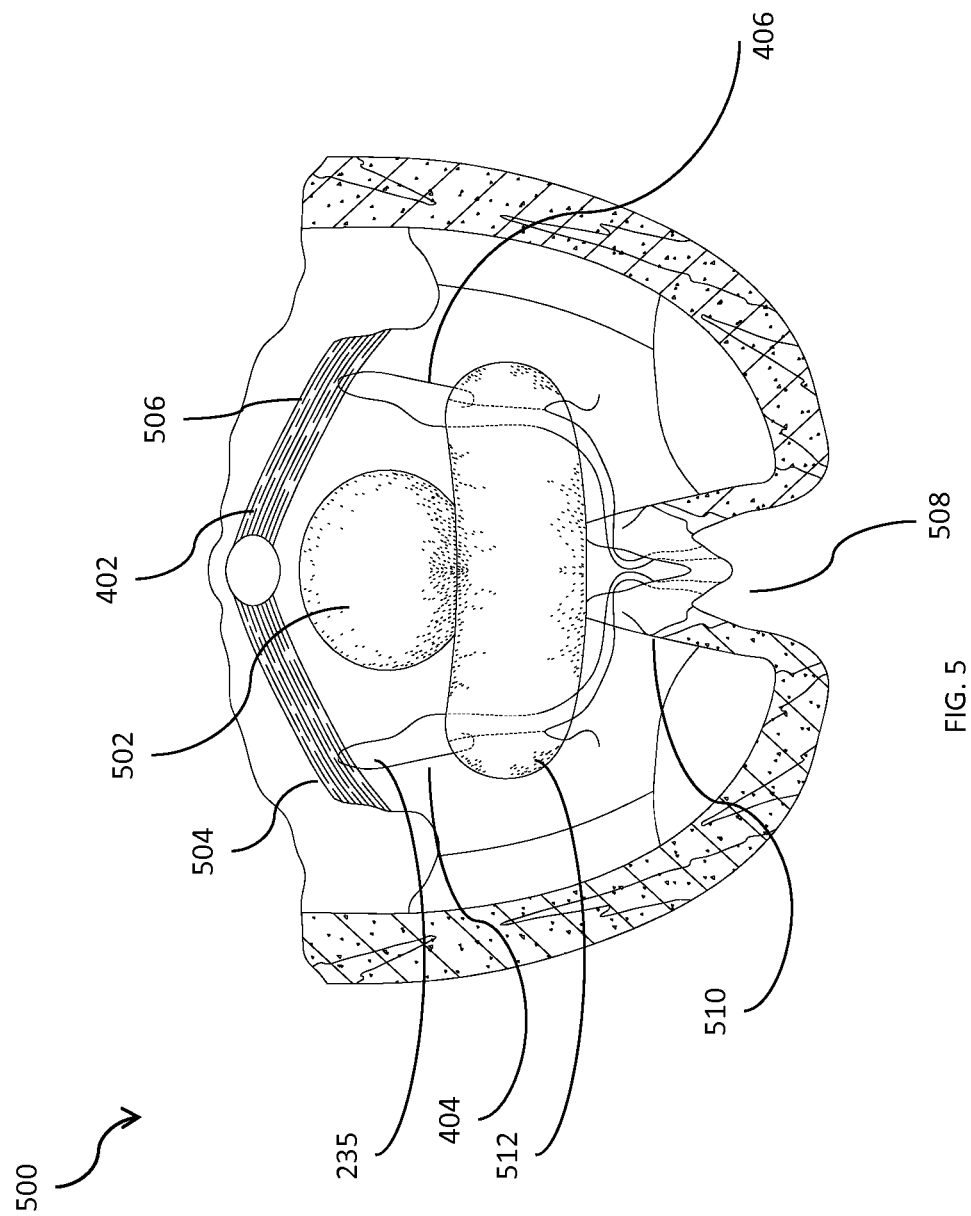
FIG. 5 illustrates a pelvic region of a patient's body where a suturing device is used, in accordance with an embodiment of the present invention.

In some embodiments of the invention, the needle 236 is coupled to a bodily implant to be placed inside the patient's body (the bodily implant illustrated in FIG. 5). In such a case, the method of operation as described above is repeated for both lateral sides of the patient's body thereby placing a second suture 406 (shown in FIG. 5) on the bodily tissue 402. In some embodiments the bodily tissue 402 where the second suture 406 is placed can be a second portion of the pelvic tissue (as explained later in FIG. 5). The first suture 404 and the second suture 406 are tensioned such that the bodily implant is positioned and affixed within the bodily tissue 402.

In a general aspect, the method of operation can include inserting at least a portion of the elongate body member 202 of the suturing device 200 coupled to at least a portion of the suture 235 into the body of the patient. The method can also include actuating the needle 236 that is slidably disposed along the lumen 226 of the elongate body member 202 such that a portion of the needle 236 is coupled to the portion of the suture 235 and is configured to move through the tissue 402 into the body of the patient.

In some embodiments, actuating can include moving the suturing device 200 in the direction A1 (illustrated in FIG. 2P). The method can include moving the needle 236 slidably disposed into the lumen 226 of the elongate body member 202 in the direction A1 along the lumen 226 of the elongate body member 202 away from the proximal portion 204 of the elongate body member 202 towards the needle receiving portion 294 of the suturing device 200 until the needle 236 has moved into the non-planar surface 213. In some embodiments, the suture 235 is loaded in the distal portion 206 of the elongate body member 102. The distal portion 206 defines the opening 214 through which the needle 236 comes out of the lumen 226 when the suturing device 200 is actuated along direction A1.

The distal portion 206 also defines the second opening 216 for receiving the tissue 402. The second opening 216 is present in between the opening 214 defined by the distal portion 206 for needle 236 to pass through and the needle receiving portion 294. In some embodiments, the suturing device 200 is placed such that the tissue 402 (to be sutured) is present between the distal portion 206 of the elongate body member 202 of the suturing device 200 and the needle receiving portion 294 of the suturing device 200.

In some embodiments, the needle receiving portion 294 comprises the non-planar surface 213. The walls 239 of this non-planar surface 213 converge to form the aperture 215. The aperture 215 acts as a capture slot for the needle 236 when it moves towards the needle receiving portion 294 on being actuated along the direction A1.

In some embodiments, the method can include engaging the needle 236 that is disposed into the lumen 226 of the elongate body member 202 with the aperture 215 formed by the walls 239 of the non-planar surface 213 present on the needle receiving portion 294 of the suturing device 200. When the needle 236 is actuated along direction A1, it passes through the second opening 216 (where the tissue 402 is placed).

In some embodiments, the radial slots 223 move to the second position 263 to provide space for the needle 236 to enter the aperture 215. In some embodiments, the needle 236 can have a dimension greater than the aperture diameter 253 of the aperture 215. When the needle 236 enters the aperture 215, the radial slots 223 move back to the first position 261, thereby capturing the needle 236 into the aperture 215. The suture 235 that is coupled to the needle 236 is thereby effectively passed through the tissue 402 (the suture 235 is coupled to the needle 236; therefore it will pass through the tissue 402 along with the needle 236). When the needle 236 is captured into the aperture 215 of the needle receiving portion 294, the suture 235 is effectively passed through the tissue 402. The needle 236 can be retrieved from the aperture 215 by sliding the needle 236 towards the enlarged portion 304 of the aperture 215. In some embodiments, the enlarged portion 304 of the aperture 215 is designed with a dimension that is greater than the dimension of the needle 236.

In some embodiments, the actuating can include moving the suturing device 200 in the direction A2. The method of operation can include moving the needle carrier 246 slidably disposed into the lumen 226 of the elongate body member 202 in the direction A2 along the lumen 226 of the elongate body member 202 towards the proximal portion 204 of the elongate body member 202 away from the needle receiving portion 294 of the suturing device 200 until the needle carrier 246 has moved into the lumen 226 of the elongate body member 202.

In some embodiments, the movement along the direction A1 moves the device into the deployed position denoted by 240. In some embodiments, the movement along direction D2 moves the device into the retracted position denoted by 238.

In some embodiments, the needle deployment mechanism 234 is disposed at least partially in the elongate body member 202. The needle deployment mechanism 234 includes the actuator 244 and a needle carrier 246. In some embodiments, the actuator 244 is configured to move the device back and forth along the direction A1 and A2.

FIG. 5 is referred to in conjunction with FIGS. 2A-2C and FIGS. 4A-4C.

Referring now to FIG. 5, a front view of a pelvic region 500 is shown that includes a representation of a uterus 502, a first part of pelvic tissue 504, a second part of pelvic tissue 506, a vagina 508, and a vaginal apex 510. This embodiment illustrates an implant assembly 512 (also referred to as bodily implant 512) that can be secured to the tissue 402 for repair of a genital prolapse that can be delivered using a suturing type delivery device (e.g., a Capio device or the suturing device 200 as described above, and the like). In some embodiments, the suture 235 is shown placed through the tissue 402 on opposite sides of the uterus 502 and the bodily implant 512 is partially drawn to the tissue 402.

In an exemplary embodiment of the invention, the tissue 402 can be a sacrospinous ligament.

Referring to FIG. 6 in conjunction with FIGS. 2A-2C, a penetration depth controller 225 is illustrated.

FIG. 6 illustrates the suturing device 200 with the penetration depth controller 225 in place being used to place the suture 235. During use, the suturing device 200 is pressed against the tissue 402 to be sutured and an adaptor 227 prevents the bodily tissue 402 from entering the second opening 216, thus controlling the depth of penetration of the needle carrier 246. In the illustrated embodiment of the invention, the penetration depth controller 225 is configured to prevent the suturing device 200 from penetrating an entire boundary of the tissue 402.

In some embodiments, the adaptor 227 is sized to control the depth of penetration (i.e., depth of bite) into the tissue 402, for example, to prevent inadvertent punctures into bones, organs, tendons, or other tissue. The adaptor 227 can be opaque, translucent, or transparent to allow for visualization in placement of the suturing device 200 onto the bodily tissue 402. In alternative embodiments, the suturing device 200 can include a plurality of adaptors that can include color coding or other markings to identify its size or penetrating depth.

Figure 7:
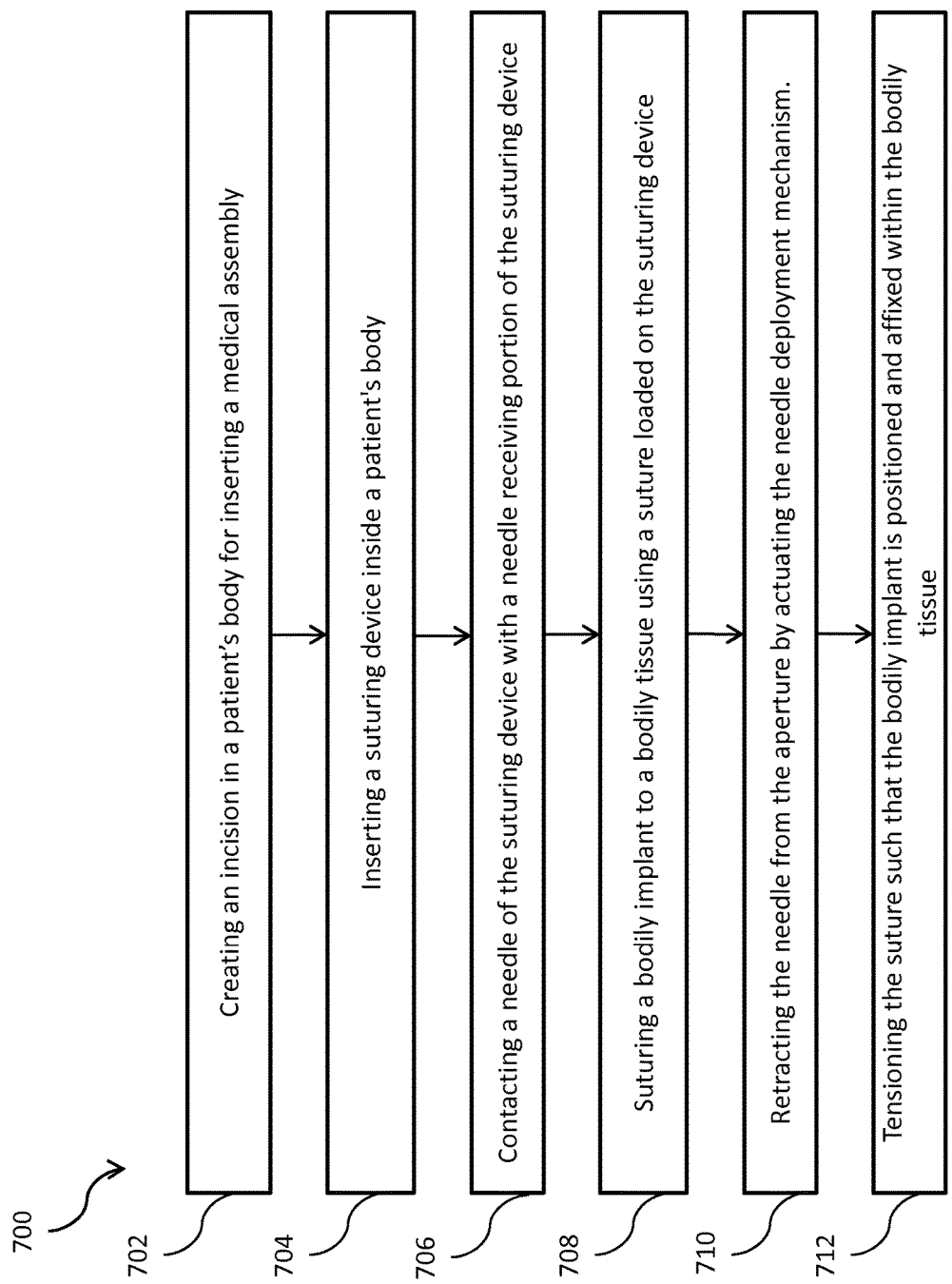
FIG. 7 illustrates a flowchart representing a method for delivery of a suture in a patient's body in accordance with an embodiment of the present invention.

FIG. 7 is a flowchart illustrating a method 700 of placement of the suture 235 using a device such as the suturing device 200, in accordance with an embodiment, of the present invention.

Referring now to FIG. 7 in conjunction with FIGS. 2A-2C, FIGS. 3A-3B, FIGS. 4A-4C and FIG. 5, the method 700 of placement of the suturing device 200 is described, in accordance with an embodiment of the present invention. The suturing device 200 is hereafter used to describe the placement in an exemplary embodiment; however, it must be appreciated that the suturing device 100 or other similar suturing devices may also be used in the similar manner.

In some embodiments, when the handle 222 or any button or switch mounted on the elongate body member 202 is pushed, the actuator 244 of the needle deployment mechanism 234 starts moving toward the deployed position 240 (along direction A1) thereby causing the needle 236 (coupled to the needle deployment mechanism 234) to exit the elongate body member 202 and move toward the needle receiving portion 294. As the operator continues to push the handle 222, the needle carrier 246 along with the needle 236 moves further and comes in contact with the needle receiving portion 294. On further actuation, the needle 236 pierces through the bodily tissue 402 and enters the needle receiving portion 294. As the handle 222 or the button is released the actuator 244 moves along the direction A2 thereby causing the needle deployment mechanism 234 and the needle 236 coupled thereto to retract. As the actuator 244 moves to the retracted position 238 the needle 236 remains in the needle receiving portion 294 and the needle carrier 246 moves out of the needle receiving portion 294 (or away from the needle receiving portion 294) and moves towards the elongate body member 202. As the actuator 244 reaches a fully refracted position, the needle carrier 246 is completely contained inside the elongate body member 202.

Having described a general overview of the method of actuation, the entire method 700 is described below.

The method 700 includes creating an incision into a patient's body for delivery of the suturing device 200 at step 702.

In accordance with some embodiments described by method 700, the suturing device 200 is inserted into the incision at 704. The suturing device 200 is placed in such a way such that the tissue 402 is positioned in the second opening 216.

The actuator 244 of the needle deployment mechanism 234 is actuated and brought to the deployed position 240 by pushing the handle 222 as explained in FIG. 3B. This causes the needle carrier 246 to push the needle 236 out of the elongate body member 202 of the suturing device 200 and pass through the tissue 402 and contact the needle receiving portion 294 of the suturing device 200 as in step 706. At step 706, the needle 236 of the suturing device 200 is contacted with the needle receiving portion 294 by actuating the needle deployment mechanism 234 such that the needle 236 moves along the non-planar surface 213 with the angled side edge 267 and into the aperture 215 of the needle receiving portion 294 and is received by the aperture 215. The needle 236 is coupled to the suture 235 at the proximal portion 237 of the needle. as explained in FIG. 3A. This coupling causes the suture 235 to pass through the tissue 402 when the needle 236 passes through the tissue 402 as in step 708.

In accordance with some embodiments of the invention, the needle 236 is guided into the aperture 215 by the non-planar surface 213 when the needle 236 contacts the needle receiving portion 294.

In accordance with some embodiments of the invention, the needle 236 is captured into the aperture 215 through the spring action of the radial slots 223 as explained in FIG. 3E. The suture 235 that is coupled to the suture needle 205 that is further coupled to the needle 236 also passes through the tissue 402. In some embodiments, when the needle 236 is captured by the aperture 215, the radial slots 223 lined onto the walls 239 of the aperture 215 close and prevent the suture 235 to enter the aperture 215. This may place the suture 235 through the tissue 402, in accordance with step 708 of method 700. At step 708, the bodily implant 512 is sutured to the tissue 402 using the suture 235 loaded on the suturing device 200. The bodily implant 512 is further coupled to the suture 235.

In accordance with some embodiments of the invention, the needle carrier 246 is brought in the retracted position 238 from the aperture 215 by actuating the needle deployment mechanism 234 at step 710.

The suture 235 is tensioned such that the bodily implant 512 is positioned and affixed within the tissue 402 at step 712.

In some embodiments of the invention, the steps described above are carried out for both lateral sides of the patient as illustrated in FIG. 5. In accordance with these embodiments, the suture 235 is a first suture 404 and the bodily tissue 402 (or simply tissue) is a first portion of the pelvic tissue 504. In such embodiments, the method 700 may include securing the first suture 404 to the first portion of the pelvic tissue such that a first part of the bodily implant 512 is disposed within the pelvic region 500 of a patient.

In some embodiments, the suture 235 is a second suture 406 and the bodily tissue 402 (or simply tissue) is a second portion of the pelvic tissue 506. In such embodiments, the method 700 may include securing the second suture 406 to the second portion of the pelvic tissue such that a second part of the bodily implant 512 is disposed within a pelvic region 500 of a patient.

In some embodiments, a suturing device includes an elongate body member, the elongate body member having a distal portion, the distal portion defining an opening; a needle deployment mechanism disposed at least partially within the elongate body member for moving a needle out of the opening at the distal portion of the elongate body member into a tissue; and a needle receiving portion, the needle receiving portion provided at the distal portion of the elongate body member to capture the needle, wherein the needle receiving portion has a non-planar surface with walls that are non-parallel with respect to a longitudinal direction of the needle receiving portion such that the walls converge to form an aperture in the needle receiving portion to receive the needle, wherein the needle receiving portion includes radial slots provided on the walls of the needle receiving portion, the radial slots being configured to move from a first position to a second position.

In some embodiments, the elongate body member includes a lumen extending from a proximal portion of the elongate body member to the opening at the distal portion of the elongate body member. In some embodiments, the needle deployment mechanism includes a needle carrier, the needle carrier defines a receiving portion configured to carry the needle, the needle is coupled to a suture.

In some embodiments, the needle carrier has a substantially circular cross-section. In some embodiments, the needle carrier is connected to an actuator, the actuator having a deployed position and a retracted position at a proximal end of the elongate body member, the needle carrier configured to exit through the opening at the distal end of the elongate body member when the actuator is in the deployed position. In some embodiments, the needle carrier is at least partially disposed into the needle receiving portion when the actuator is in the deployed position.

In some embodiments, the suturing device includes a handle configured to be held by an operator, the actuator is disposed on the handle and is configured to actuate the needle deployment mechanism externally from a patient's body.

In some embodiments, the radial slots of the needle receiving portion are configured to move from the first position to the second position thereby allowing the aperture to open and allow entry of the needle. In some embodiments, the radial slots of the needle receiving portion are configured to move from the first position to the second position to allow closing of the aperture after the needle has entered the aperture, wherein closing of the aperture configured to capture a distal portion of the needle within the aperture. In some embodiments, the needle receiving portion is made out of a flexible material configured to flexibly open or close the aperture based on a push or pull force exerted by the needle on the aperture. In some embodiments, the needle receiving portion includes a penetration depth controller to control penetration depth of the needle. In some embodiments, the non-planar surface is a conical surface. In some embodiments, the needle receiving portion includes more than one aperture placed adjacent to one another.

In some embodiments, a suturing device includes an elongate body member, the elongate body member having a proximal portion, a distal portion, the distal portion defining an opening, the elongate body member defining a lumen from the proximal portion to the opening; a needle deployment mechanism disposed at least partially within the elongate body member, the needle deployment mechanism including: a needle carrier disposed at the distal portion of the elongate body member and defining a channel for holding a needle; and an actuator configured to move the needle out of the opening at the distal portion of the elongate body member into a tissue; and a needle receiving portion, the needle receiving portion provided at the distal portion of the elongate body member to capture the needle, wherein the needle receiving portion has a non-planar surface with walls that are non-parallel with respect to a longitudinal direction of the needle receiving portion such that the walls converge to form an aperture in the needle receiving portion to receive the needle, wherein the needle receiving portion includes radial slots provided on the walls of the needle receiving portion, the radial slots being configured to move from a first position to a second position.

In some embodiments, a method includes inserting a suturing device inside a patient's body, the suturing device including an elongate body member, a needle deployment mechanism disposed at least partially within the elongate body member, and a needle receiving portion; contacting a needle of the suturing device with the needle receiving portion by actuating the needle deployment mechanism such that the needle moves along a non-planar surface and into an aperture of the needle receiving portion and is received by the aperture, wherein the non-planar surface has walls that are non-parallel with respect to a longitudinal direction of the needle receiving portion and radial slots provided on the walls of the needle receiving portion, the radial slots being configured to move from a first position to a second position; suturing a bodily implant to a bodily tissue using a suture loaded on the suturing device, the bodily implant further coupled to the suture; and retracting the needle from the aperture by actuating the needle deployment mechanism.

In some embodiments, the method includes creating an incision in a patient's body for inserting the suturing device. In some embodiments, the suture is a first suture and the bodily tissue is a first portion of a pelvic tissue, the suturing further includes securing the first suture to the first portion of the pelvic tissue such that a first part of the bodily implant is disposed within a pelvic region of a patient. In some embodiments, the suturing further includes securing a second suture to a second portion of the pelvic tissue such that a second part of the bodily implant is disposed within the pelvic region of a patient.

In some embodiments, the method includes tensioning the suture such that the bodily implant is positioned and affixed within the bodily tissue. In some embodiments, the non-planar surface is a conical surface.

While the invention has been disclosed in connection with the preferred embodiments shown and described in detail, various modifications and improvements thereon will become readily apparent to those skilled in the art. Accordingly, the spirit and scope of the present invention is not to be limited by the foregoing examples, but is to be understood in the broadest sense allowable by law.

What is claimed is:

1. A suturing device comprising:
an elongate body member, the elongate body member having a distal portion, the distal portion defining an opening;
a needle carrier disposed at least partially within the elongate body member, the needle carrier being configured to move a needle out of the opening at the distal portion of the elongate body member and into a tissue; and
a needle receiving portion configured to capture the needle, the needle receiving portion including a non-planar member,
the non-planar member includes a non-planar surface with walls that are non-parallel with respect to a longitudinal direction of the needle receiving portion such that the walls converge to form an aperture in the needle receiving portion to receive the needle, wherein convergence of the walls defines a decreasing diameter of the aperture, the needle receiving portion includes radial members provided on the walls of the non-planar member, the radial members being configured to move from a first position to a second position to allow the aperture to open and allow entry of the needle, the aperture includes an enlarged portion configured to allow the needle to be removed from the aperture.

2. The suturing device of claim 1, wherein the elongate body member includes a lumen extending from a proximal portion of the elongate body member to the opening at the distal portion of the elongate body member.

3. The suturing device of claim 1, wherein the needle carrier defines a needle carrier receiving portion configured to carry the needle, the needle being coupled to a suture.

4. The suturing device of claim 3, wherein the needle carrier is connected to an actuator, the actuator having a deployed position and a retracted position at a proximal end of the elongate body member, the needle carrier configured to exit through the opening at a distal end of the elongate body member when the actuator is in the deployed position.

5. The suturing device of claim 4, wherein the needle carrier is at least partially disposed into the needle receiving portion when the actuator is in the deployed position.

6. The suturing device of claim 1, wherein the radial members of the needle receiving portion are configured to move from the second position to the first-position to allow closing of the aperture after the needle has entered the aperture, wherein closing of the aperture is configured to capture a distal portion of the needle within the aperture.

7. The suturing device of claim 1, wherein the needle receiving portion is made out of a flexible material configured to flexibly open or close the aperture based on a push or pull force exerted by the needle on the aperture.

8. The suturing device of claim 1, wherein the needle receiving portion includes a penetration depth controller to control penetration depth of the needle.

9. The suturing device of claim 1, wherein the non-planar surface is a conical surface.

10. The suturing device of claim 1, wherein the needle receiving portion includes more than one aperture placed adjacent to one another.

11. The suturing device of claim 1, wherein the diameter of the convergence of the walls gradually decrease to form the aperture formed at the bottom of the non-planar surface.

12. A suturing device comprising:
an elongate body member, the elongate body member having a proximal portion, a distal portion, the distal portion defining an opening, the elongate body member defining a lumen from the proximal portion to the opening;
a needle deployment mechanism disposed at least partially within the elongate body member, the needle deployment mechanism including:
a needle carrier disposed at the distal portion of the elongate body member and defining a channel for holding a needle; and
an actuator configured to move the needle out of the opening at the distal portion of the elongate body member into a tissue; and
a needle receiving portion including a non-planar member, the needle receiving portion provided at the distal portion of the elongate body member to capture the needle, wherein the non-planar member has a non-planar surface with walls that are non-parallel with respect to a longitudinal direction of the needle receiving portion such that the walls converge to form an aperture in the needle receiving portion to receive the needle, the aperture defines a distal end that includes an enlarged portion, wherein convergence of the walls defines a decreasing diameter of the aperture, wherein the needle receiving portion includes radial members provided on the walls of the non-planar member, the radial members being configured to move from a first position to a second position to allow the aperture to open and allow entry of the needle, the enlarged portion of the aperture being sized to allow the needle to pass through,
wherein the needle receiving portion includes a groove such that the non-planar member is configured to slide within the groove in a first direction and a second direction.

13. The suturing device of claim 12, wherein the first direction is substantially opposite to the second direction.

14. A method comprising:
inserting a suturing device inside a patient's body, the suturing device including an elongate body member, a needle deployment mechanism disposed at least partially within the elongate body member, and a needle receiving portion coupled to the elongate body;
contacting a needle of the suturing device with the needle receiving portion by actuating the needle deployment mechanism such that the needle moves along a non-planar member and into an aperture of the needle receiving portion and is received by the aperture, the aperture defines a distal end that includes an enlarged portion, wherein the non-planar member includes a non-planar surface with walls that are non-parallel with respect to a longitudinal direction of the needle receiving portion to form the aperture in the needle receiving portion, the needle receiving portion includes radial members provided on the walls of the non-planar member, wherein convergence of the walls defines a decreasing diameter of the aperture, the radial members being configured to move from a first position to a second position to allow the aperture to open and allow entry of the needle, wherein the needle receiving portion includes a groove such that the non-planar member is configured to slide within the groove in a first direction and a second direction; and
suturing a bodily implant to a bodily tissue using a suture loaded on the suturing device, the bodily implant further coupled to the suture; and
retracting the needle from the aperture by actuating the needle deployment mechanism.

15. The method of claim 14 further comprising creating an incision in a patient's body for inserting the suturing device.

16. The method of claim 14, wherein the suture is a first suture and the bodily tissue is a first portion of a pelvic tissue, the suturing further comprising:
securing the first suture to the first portion of the pelvic tissue such that a first part of the bodily implant is disposed within a pelvic region of a patient.

17. The method of claim 16, wherein the suturing further comprises:
securing a second suture to a second portion of the pelvic tissue such that a second part of the bodily implant is disposed within the pelvic region of the patient.

18. The method of claim 14, further comprising:
tensioning the suture such that the bodily implant is positioned and affixed within the bodily tissue.

19. The method of claim 14, wherein the non-planar surface is a conical surface.

* * * * *